US006828471B2

(12) United States Patent
Sawyers et al.

(10) Patent No.: US 6,828,471 B2
(45) Date of Patent: Dec. 7, 2004

(54) MICE MODELS OF HUMAN PROSTATE CANCER

(75) Inventors: Charles L. Sawyers, Los Angeles, CA (US); Karen A. Klein, Los Angeles, CA (US); Owen N. Witte, Sherman Oaks, CA (US); Robert E. Reiter, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/062,925

(22) Filed: Jan. 30, 2002

(65) Prior Publication Data

US 2002/0133833 A1 Sep. 19, 2002

(Under 37 CFR 1.47)

Related U.S. Application Data

(63) Continuation of application No. 09/567,202, filed on May 8, 2000, now Pat. No. 6,365,797, which is a division of application No. 08/951,143, filed on Oct. 15, 1997, now Pat. No. 6,107,540, which is a continuation-in-part of application No. 08/732,676, filed on Oct. 15, 1996, now abandoned.

(51) Int. Cl.$^7$ ...................... A01K 67/00; A01K 67/033; A01K 67/027
(52) U.S. Cl. ................... 800/10; 800/8; 800/18
(58) Field of Search ................... 800/8, 10, 18

(56) References Cited

PUBLICATIONS

Aldrovandi, Grace M. et al., "The SCID–hu Mouse as a Model for HIV–1 Infection," *Nature*, Jun. 24, 1993, 363:732–6 (Exhibit 9).

Batson, Oscar V., "The Role of the Vertebral Veins in Metastatic Processes," *Ann. Int. Med.*, 1942, 16:38–45 (Exhibit 10).

Berrettoni, Beth A. and John R. Carter, "Current Concepts Review Mechanisms of Cancer Metastasis to Bone," *The Journal of Bone and Joint Surgery*, 1986, 68A:308–312. (Exhibit 11).

Brandt, Burkhard et al., "Isolation of Prostate–Derived Single Cells and Cell Clusters From Human Peripheral Blood," *Cancer Research*, Oct. 15, 1996, 56:4556–61. (Exhibit 12).

Coman, Dale Rex and Robert P. DeLong, "The Role of the Vertebral Venous System in the Metastasis of Cancer to the Spinal Column," *Cancer*, 1951, 4:610–8. (Exhibit 13).

Deguchi, T. et al., "Detection of Micrometastatic Prostate Cancer Cells in the Bone Marrow of Patients with Prostate Cancer," *British Journal of Cancer*, 1997, 75(5):634–8. (Exhibit 14).

Ellis, William J. et al., "Characterization of a Novel Androgen–Sensitive, Prostate–Specific Antigen–Producing Prostatic Carcinoma Xenograft: LuCap 23," *Clinical Cancer Research*, Jun. 1996, 2:1039–48. (Exhibit 15).

Fidler, Isaiah J., "Critical Factors in the Biology of Human Cancer Metastasis: Twenty–Eight G.H.A Clowes Memorial Award Lecture," *Cancer Research*, Oct. 1, 1990, 50:6130–8. (Exhibit 16).

Ghossein, Ronald A. et al., "Detection of Circulating Tumor Cells in Patients with Localized and Metastatic Prostatic Carcinoma: Clinical Implications," *Journal of Clinical Oncology*, May 1995, 13(5):1195–200. (Exhibit 17).

Gleave, Martin E. et al., "Serum Prostate Specific Antigen Levels in Mice Bearing Human Prostate LNCaP Tumors are Determined by Tumor Volume and Endocrine and Growth Factros," *Cancer Research*, Mar. 15, 1992, 52:1598–605. (Exhibit 18).

Haq, Mahmudul et al., "Rat Prostate Adenocarcinoma Cells Disseminate to Bone and Adhere Preferentially to Bone Marrow–Derived Endothelial Cells," *Cancer Research*, Sep. 1, 1992, 52:4613–9. (Exhibit 19).

Hsieh, J.T. et al., "An Androgen–Independent Model of Human Prostate Cancer Progression: Molecular and Cellular Characterization," *Proceedings of the American Association for Cancer Research*, Mar. 1993, 34:248. (Exhibit 20).

Hsu, Su–Ming et al., "A Comparative Study of the Peroxidase–Antiperoxidase Method and an Avidin–Biotin Complex Method for Studying Polypeptide Hormones with Radioimmunoassay Antibodies," *American Society of Clinical Pathologists*, 1981, 75:734–8. (Exhibit 21).

Karp, Judith E. et al., "Prostate Cancer Prevention: Investigational Approaches and Opportunities," *Cancer Research*, Dec. 15, 1996, 56:5547–56. (Exhibit 22).

Katz, Aaron E. et al., "Molecular Staging of Prostate Cancer with the Use of an Enhanced Reverse Transcriptase–PCR Assay," *Urology*, Jun. 1994, 43(6):765–75. (Exhibit 23).

Kjønniksen, Inge et al., "Validity and Usefulness of Human Tumor Models Established by Intratibial Cell Inoculation in Nude Rats," *Cancer Research*, Apr. 1, 1994, 54:1715–9. (Exhibit 24).

Kozlowski, James M. et al., "Prostate Cancer and the Invasive Phenotype: Application of New In Vivo and In Vitro Approaches," *Tumor Progression and Metastasis*, 1988, 189–231, (Exhibit 25).

(List continued on next page.)

*Primary Examiner*—Deborah Crouch
*Assistant Examiner*—Thaian N. Ton
(74) *Attorney, Agent, or Firm*—Townsend and Townsend and Crew LLP

(57) ABSTRACT

The present invention provides an immune deficient mouse having a human prostate xenograft of locally advanced or metastatic prostate cancer and uses thereof.

6 Claims, 10 Drawing Sheets

OTHER PUBLICATIONS

Marcelli, Marco et al., "Definition of the Human Androgen Receptor Gene Structure Permits the Identification of Mutations that Cause Androgen Resistance: Premature Termination of the Receptor Protein at Amino Acid Residue 588 Causes Complete Androgen Resistance," *Molecular Endocrinology*, 1990, 909:1105–16. (Exhibit 26).

Melchior, Sebastian W. et al., "Clinical Relevance of Prostate Cells in the Bone Marrow of Patients with Clinically Localized Carcinoma of the Prostate (CAP)," *The Journal of Urology*, 1997, 157:1718. (Exhibit 27).

Nagabhushan, Moolky et al., "CWR22: The First Human Prostate Cancer Xenograft with Strongly Androgen–Dependent and Relapsed Strains Both In Vivo and in Soft Agar," *Cancer Research*, Jul. 1, 1996, 56:3042–6. (Exhibit 28).

Netland, Peter A. and Bruce R. Zetter, "Metastatic Potential of B16 Melanoma Cells after In Vitro Selection for Organ–specific Adherence," *The Journal of Cell Biology*, Sep. 1985, 101:720–4. (Exhibit 29).

Nishijima, Yukiko et al., "Clinical Significance of the Vertebral Vein in Prostate Cancer Metastasis," *Adv. Exp. Med. Biol.*, 1992, 324:93–100. (Exhibit 30).

Noel, A. et al., "Basement Membrane Components (Matrigel) Promote the Tumorgenicity of Human Breast Adenocarcinoma MCF7 Cells and Provide an In Vivo Model to Assess the Responsiveness of Cells to Estrogen," *Biochemical Pharmacology*, 1992, 43(6):1263–7. (Exhibit 31).

Pang, Shen et al., "Prostate Tissue Specificity of the Prostate–Specific Antigen Promoter Isolated from a Patient with Prostate Cancer," *Human Gene Therapy*, Nov. 1995, 6:1417–26. (Exhibit 32).

Saiki, Randall K. et al, "Enzymatic Amplification of Beta–Globulin Genomic Sequences and Restriction Site Analysis for Diagnosis of Sickle Cell Anemia," *Science*, 1895, 230:1350–4. (Exhibit 33).

Seiden, Michael V. et al., "Detection of Circulating Tumor Cells in Men with Localized Prostate Cancer," *Journal of Clinical Oncology*, Dec. 1994, 12(12):2634–9. (Exhibit 34).

Sutherland, Richard W. et al., "Androgen Receptor Gene Mutations are Rarely Associated with Isolated Penile Hypospadias," *The Journal of Urology*, 1996, 156:828–31. (Exhibit 35).

Thalmann, George N. et al., "Androgen–Independent Cancer Progression and Bone Metastasis in the LNCaP Model of Human Prostate Cancer," *Cancer Research*, May 15, 1994, 54:2577–81. (Exhibit 36).

Wang, Min and Mark E. Stearns, "Isolation and Characterization of PC–3 Human Prostatic Tumor Sublines Which Preferentially Metastasize to Select Organs in S.C.I.D. Mice," *Differentiation*, 1991, 48:115–25. (Exhibit 37).

Wood, David P. Jr. et al, "Identification of Bone Marrow Micrometastases in Patients with Prostate Cancer," *Cancer*, 1994, 74:2533–40. (Exhibit 38).

Wu, His–Chin et al., "Derivation of Androgen–Independent Human LNCaP Prostatic Cancer Cell Sublines: Role of Bone Stromal Cells," *Int. J. Cancer*, 1994, 57:406–12. (Exhibit 39).

Zetter, Bruce R. et al., "The Cellular Basis for Prostate Cancer Metastasis," *Adv. Exp. Med. Biol.*, 1992, 324:39–43. (Exhibit 40).

Liu, A. Y., et al., "Prostatic Cell Lineage Markers: Emergence of $BCL2^+$ Cells of Human Prostate Cancer Xenograft LuCaP 23 Following Castration," *Int. J. Cancer*, 65:85–89 (1996).

Lubaroff, D. M., et al., "Survival of Human Prostate Carcinoma, Benign Hyperplastic Prostate Tissues, and IL–2–Activated Lymphocytes in SCID Mice," *The Prostate*, 27:32–41 (1995).

Wainstein, M. A., et al., "CWR22: Androgen–Dependent Xenograft Model Derived from a Primary Human Prostatic Carcinoma," *Cancer Research*, 54:6049–6052 (1994).

Pretlow, T. G., et al., "Xenografts of Primary Human Prostatic Carcinoma," *Journal of the National Cancer Institute*, 85(5):394–398 (1993).

Pretlow, T. G., et al., "Transplantation of Human Prostatic Carcinoma into Nude Mice in Matrigel," *Cancer Research*, 51:3814–3817 (1991).

Perez–Stable et al., *Cancer Research*, vol. 57, pp. 900–906. (Mar. 1, 1997).

Sato et al., *Journal of Urology*, vol. 155: 5, p. 338A. (May 4, 1996).

Van Weerden et al., *American Journal of Pathology*, vol. 149: 3, pp. 1055–1062, (Sep. 1996).

control　　　8 weeks　　　LAPC 4

MICE MODELS OF HUMAN PROSTATE CANCER

This application is a continuation of U.S. Ser. No. 09/567,202, filed May 8, 2000, now U.S. Pat. No. 6,365,797; which is a divisional of U.S. Ser. No. 08/951,143, filed Oct. 15, 1997, now U.S. Pat. No. 6,107,540: which is a CIP of U.S. Ser. No. 08/732,676, filed Oct. 15, 1996, now abandoned. The foregoing applications are incorporated herein by reference.

Throughout this application, various publications are referenced within parentheses. Full citations of these publications may be found at the end of the specification immediately preceding the claims. The disclosures of these publications are hereby incorporated by reference herein in their entireties.

BACKGROUND OF THE INVENTION

Prostate cancer is the most common cause of cancer in men. In 1996; 317,000 new cases of prostate adenocarcinoma were diagnosed and over 41,400 men died of the disease (Karp et al., 1996). Only lung cancer has a higher mortality. The chance of a man developing invasive prostate cancer during his lifetime is 1 in 6 or 15.4% At the age of 50, a man has a 42% chance of developing prostate cancer and 2.9% of dying from the disease. While advances in early diagnosis and treatment of locally confined tumors have been achieved, prostate cancer is incurable once it has metastasized. Patients with metastatic prostate cancer on hormonal therapy will eventually develop an androgen-refractory (androgen independent) state that will lead to disease progression and death.

The major cause of morbidity and mortality from prostate cancer is the result of androgen-independent metastatic tumor growth. As a result, there is great interest in defining the molecular basis for advanced staged disease with the hope that these insights may improve the therapeutic options for these patients. However, progress in this area has been difficult for a number of reasons. For example, the availability of prostate tissue for molecular studies is limited because most prostate tumors are small. Moreover, there is tremendous heterogeneity within surgical prostatectomy tumor samples, it is difficult to reducibly culture prostate cancer explants in vitro, and there are a limited number of immortalized prostate cancer cell lines.

There is, therefore, an interest in finding alternative procedures which will allow for stable growth of prostate cancer tissue, which in turn would allow for the investigation of the progression of prostate cancer in vivo, provide a stable supply of prostate cancer tissue and provide a model for metastatic expansion of prostate cancer which accurately simulates or mimics the biology of the disease.

There is also a need for more reliable and informative staging and prognostic methods in the management of advanced prostate cancer. Clinically staging prostate tumors relies on rectal examination to determine whether the tumor remains within the borders of the prostatic capsule (locally confined) or extends beyond it (locally advanced), in combination with serum PSA determinations and transrectal ultrasound guided biopsies. However, none of these techniques has proven reliable for predicting progression of the disease.

The primary sites of prostate cancer metastasis are the regional lymph nodes and bone. Bone metastases occur in sites of hematopoietically active red bone marrow, including lumbar vertebral column, ribs, pelvis, proximal long bones, sternum and skull. Bony metastases of prostate cancer differ from those of other tumors that commonly colonize in bone in that they are characterized by a net gain in bone formation (osteoblastic) rather than resorption predominant in bone metastases of breast cancer and melanoma.

Until recently, bone metastasis was thought to be a late stage in disease progression. However, the recent development of highly sensitive techniques (such as RT-PCR for prostate specific genes) to detect prostate cancer cells has revised this notion. Prostate cancer cells have been detected in the peripheral blood and bone marrow of patients with advanced stage disease using RT-PCR assays for PSA mRNA (Ghossein et al., 1995; Seiden et al., 1994; Wood et al., 1994; Katz et al., 1994) or immunomagnetic bead selection for PSA protein (Brandt et al., 1996). When positive, these tests show that prostate cancer cells represent about 0.1–1.0% of the circulating blood cells. Moreover, it is now clear that small numbers of prostate cancer cells circulate in the peripheral blood and lodge in the bone marrow even in patients with early stage, low risk disease (Olsson et al., 1997; Deguchi et al., 1997; Katz et al., 1996). Interestingly, these cells tend to disappear in most patients following radical prostatectomy (Melchior et al., 1997). These results suggest that the primary tumor site is a constant source for seeding the marrow, and that only a small subset of these cells have the capacity to grow into a metastatic lesion. This concept is consistent with estimates from animal models for other tumor types that only about 1 in 10,000 circulating cancer cells are able to lodge in and productively colonize other organs (Fidler et al., 1990).

The factors involved in advanced prostate cancer progression to bone metastasis are poorly defined. Anatomic, local bone/marrow and tumor cell factors are all believed to play a role. Baston described the extensive vertebral venous system that consists of a network of longitudinal, valveless veins that run parallel to the vertebral column and form extensive, direct anastomoses with the veins of the ribs, pelvis and brain (Baston, 1942). Prostate cancer cells entering prostatic veins may be transported via this plexus directly to these organs without entering the inferior vena cava of passing through the lungs. This hypothesized mechanism of metastasis both by clinical documentation of patterns of prostate cancer metastasis compared to other tumors and by animal models wherein occlusion of inferior vena cava during tail vein injection of tumor cells increased the incidence of vertebral metastasis (Nishijima et al., 1992; Coman and DeLong, 1951).

Although the vascular anatomy is an essential component of the spread of prostate cancer to bone, it cannot fully explain the selective pattern of all skeletal metastases. Bone, which receives 5–10% of the cardiac output, is a more frequent metastatic site than would be expected from blood-flow criteria (Berettoni and Carter, 1986). Bone marrow consists of two clearly identifiable components: the hematopoetic cells which comprise the majority of the cellular elements, and stromal component that is formed of highly vascular connective tissue. The hematopoetic cells are transient in the bone marrow; upon maturation they move into the blood stream. The stroma, however remains and serves as a scaffolding upon which the hematopoetic cells can differentiate and mature. One of the important factors in prostate cancer cells arresting in these sites is likely their adhesion to the bone marrow stroma. It has been demonstrated both in vitro and in vivo that tumor cells will preferentially adhere to the stromal cells of the organs to which they metastasize (Haq et al., 1992; Netland and Zetter, 1985; Zetter et al., 1992). When rat prostate cancer (MatLyLu) cells were injected into the left ventricle of syngenic rats, vertebral body metastases developed: these metastases were then collected, disaggregated and reinjected. Cell lines established after 6 similar passages through animals adhered strongly and preferentially to bone marrow stroma and endothelial cells (Haq et al, 1992). A similar approach has increased the incidence of metastasis from the LNCaP prostate cancer cell line in immune deficient mice (Thalmann et al., 1994).

It is critical that appropriate in vivo models for prostate cancer bone metastasis be developed to more fully explore the mechanistic aspects of this process. To date, most work in this area has focused on three human prostate cancer cell lines -PC-3, DU-145, and LNCaP (Lee et al., 1993). All three grow a subcutaneous nodules in immune deficient mice, and sublines with variable metastatic properties have been derived (Shervin et al., 1988, 1989; Wang and Sterarns, 1991; Kozlowski et al., 1988). However, none of these sublines has been shown to reproducibly give rise to osteoblastic lesions typical of prostate cancer. A major limitation of the DU-145 and PC-3 cell lines is the lack of prostate specific antigen (PSA) and androgen receptor (AR) expression (Kaighn et al., 1979; Gleave et al., 1992), which raises regarding relevance to clinical prostate cancer. The LNCaP cell line is androgen responsive and expresses PSA, but contains a mutation in the androgen receptor which alters ligand specificity.

SUMMARY OF THE INVENTION

The invention provides animal xenograft models of human prostate cancer progression capable of simulating or mimicking the development of primary tumors, micrometastasis, and the formation of osteoblastic lesions characteristic of late stage disease. The model may be used to study the stagewise progression of prostate cancer. In this regard, the invention replicates the process of cell migration from the primary tumor site to distant sites of micrometastasis, including bone marrow, as well as the development of macrometastatic osteoblastic bone lesions from micrometastatic precursors. The models are also capable of duplicating the clinical transition from androgen dependent to androgen independent tumor growth characteristic of advanced prostate cancer patients undergoing androgen ablation therapy. In addition, methods for propagating prostate cancer cells within the various stages of prostate cancer as well as methods for isolating and expanding stage-specific prostate cancer cell populations are also provided. Further, the invention provides a unique, serially-passaged, androgen-sensitive prostate cancer cell line which expresses PSA, wild-type androgen receptor, and prostate acid phosphatase. The models and methods of the invention provide a system for studying the molecular biology of prostate cancer evaluating the influence that various genes and therapeutic compounds have on distinct stages of disease progression, assessing the metastatic potential of prostate cancer cells, and designing patient-specific therapeutic regimens.

BRIEF DESCRIPTION OF THE FIGURES

FIG. 1A: DNA-PCR analysis of genomic DNA isolated from xenografts using primers specific for the human β-globin gene. Each sample shown was obtained from late passage xenografts. The LAPC-5 sample was obtained at passage 4 when the human tumor was overgrown by a tumor of murine origin. The two LAPC-4 samples were obtained from androgen dependent ("ad") and androgen independent ("ai") sublines FIG. 1B: RT-PCR analysis of total RNA using primers specific for human PSA and human or murine β-actin ("% human cells" refers to the percent of LNCaP cells which are diluted into $10^5$ mouse cells). A dilution series of human prostate cancer LNCaP cells into murine NIH 3T3 cells is shown on the left side of the figure, with the percentage of LNCaP cells varying from 100% to 0.0%. The results from the three LAPC xenografts are shown on the right.

FIG. 4A: Line graph showing typical results from two animals in the cohort whose tumor sizes were equivalent at 4 weeks. The time course for tumor development in a female mouse is shown for comparison. FIG. 4B: Bar graph showing the average tumor size (+/- standard error) from the entire cohort of intact and castrated male mice. The data from each animal are expressed as tumor size relative to the 4 week time point.

DETAILED DESCRIPTION OF THE INVENTION

Immune Deficient Animal Hosts

Figure 1:
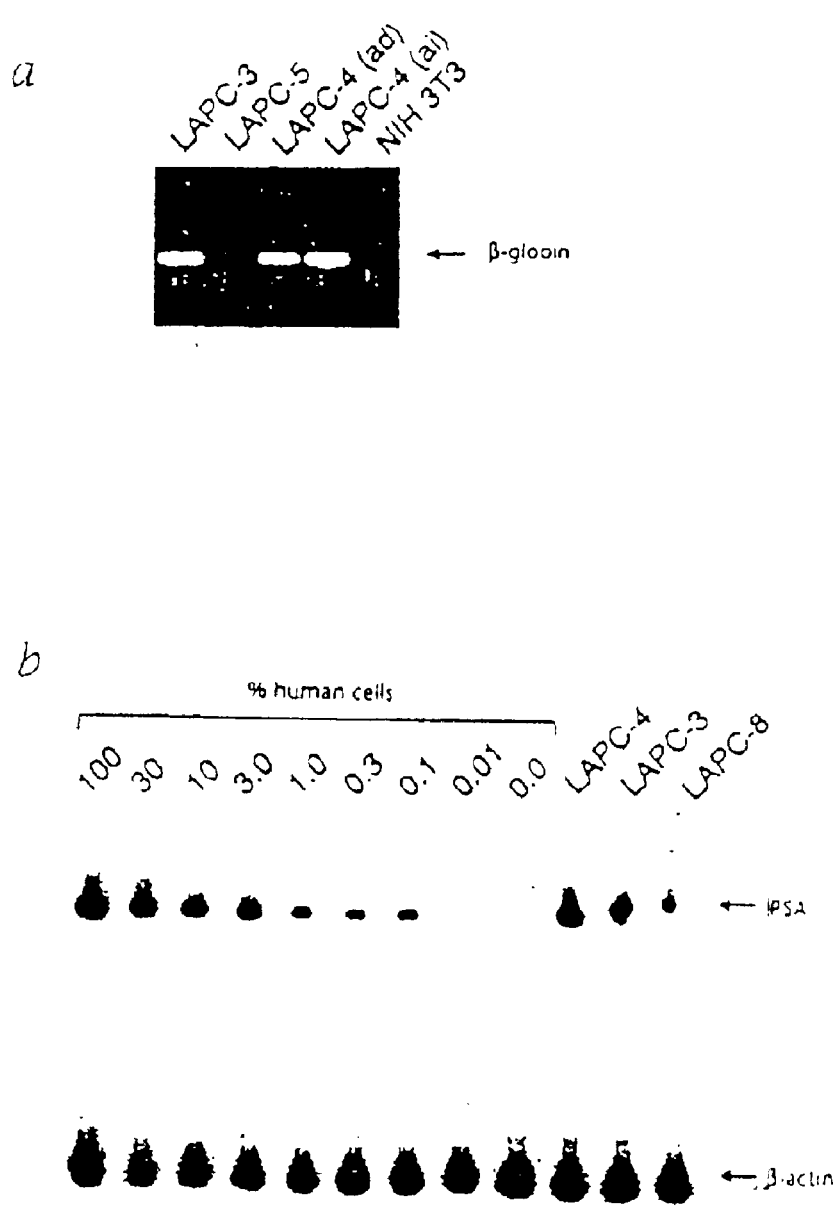
FIG. 1. Molecular analysis of prostate cancer xenografts for human DNA content and expression of prostate specific antigen (PSA).

Severe combined immune deficient (SCID) mice are the preferred animal host utilized in the practice of the invention. Various other immune deficient mice, rodents or animals may be used, including those which are deficient as a result of a genetic defect, which may be naturally occurring or induced, such as, for example, nude mice, Rag 1 and/or Rag 2 mice, and the like, and mice which have been cross-bred with these mice and have an immunocompromised background. The deficiency may be, for example, as a result of a genetic defect in recombination, a genetically defective thymus or a defective T-cell receptor region. Induced immune deficiency may be as a result of administration of an immunosuppressant, e.g. cyclosporin, removal of the thymus, etc. Various transgenic immune deficient mice are currently available or can be developed in accordance with conventional techniques. Ideally, the immune deficient mouse will have a defect which inhibits maturation of lymphocytes, particularly lacking the ability to rearrange the T-cell receptor region. Female, male, castrated or uncastrated mice may be employed, depending upon whether one is interested in studying the effect of the availability of androgens on the course of the tumor growth. In the particular and preferred embodiments described herein, C.B. 17 scid/scid mice are used. In addition to mice, immune deficient rats or similar rodents may also be employed in the practice of the invention.

Models that Simulate Advanced Prostate Cancer

One aspect of the invention provides murine xenograft models which simulate or mimic human prostate cancer from primary tumor formation. Also provided are methods for propagating advanced stage human prostate tumor tissue as subcutaneous xenografts in immune deficient mice. In the practice of the invention, prostate cancer xenografts may be established in immune deficient mice by the subcutaneous implantation of fresh human prostate cancer explants surgically removed from patients with locally advanced or metastatic prostate cancer. The site of implantation may be into any subcutaneous site which will permit blood supply to reach the implant, such as the flanks of the host animal. Tissue from primary prostate tumors as well as from sites of lymph node, lung, bone, and other organ metastases may be used to establish the prostate cancer xenografts of the invention. Prostate tumor explants may be introduced in conjunction with a basement membrane composition, such as Matrigel (U.S. Pat. No. 5,508,188). an extracellular matrix preparation which has been shown to enhance the growth of epithelial tumors in vivo (including prostate cancer cells)(Lim et al., 1993; Noel et al. 1992; Pretlow et al., 1991), as well as other similar types of compositions. Once established, the xenograft tumors grow to considerable size, providing substantial tissue volumes for further use. Xenografts of the invention retain the human phenotype as determined by human β-globin expression, express human prostate specific antigen (PSA), and retain androgen sensitivity and metastatic growth characteristics reflective of the clinical situation.

As used herein, the term "locally advanced prostate cancer" and "locally advanced disease" mean prostate cancers which have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e. resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

This and other aspects of the invention described herein provide tools for studying the pathogenesis and treatment of advanced prostate cancer. For example, immune deficient mice bearing subcutaneous (and other) xenografts may be used to evaluate the effect of various prostate cancer treatments (e.g., therapeutic compositions, gene therapies, immunotherapies, etc.) on the growth of tumors and progression of disease. Xenograft cells may be used to identify novel genes and genes which are differentially expressed in prostate cancer cells, or to analyze the effect such genes have on the progression of prostate cancer. For example, the genetic compositions of prostate cancer cells from xenografts having differing androgen sensitivities (e.g., androgen dependent vs. androgen independent) may be compared to each other as well as to the genetic compositions of normal prostate cells. Likewise, the genetic compositions of micrometastatic prostate cancer cells may be compared to those of metastatic prostate cancer cells. Various nucleic acid subtraction and sampling techniques may be used for this purpose, including, for example, representational difference analysis (RDA). In addition, prostate cancer xenograft cells may be used for the introduction of various genetic capabilities, including the introduction of various genes, antisense sequences, ribozymes, regulatory sequences which enhance or repress the expression of endogenous genes, and so forth.

In addition, this aspect of the invention provides methods for purifying prostate cancer cells from the heterogeneous mixture of cells typical of human prostate cancer biopsy material, further providing methods for generating greater quantities of tumor cells for subsequent use and analysis. In one embodiment, the method for purifying prostate cancer cells comprises implanting human prostate cancer biopsy material subcutaneously into a SCID or other immune deficient mouse and allowing the implanted material to grow as a xenograft in the mouse. The purified human prostate cancer cells are obtained by harvesting the xenograft. Xenografts may be expanded and further purified by serial propagation in additional immune deficient mice or by propagation in short term cell culture. Single cell suspensions of xenograft tumor tissue or cultured cells may be used to orthotopically seed intraprostatic tumors, bone tumors or other organ tumors. Xenograft tumor tissue and cell preparations may be frozen and viably recovered for later use.

The invention also provides subcutaneous prostate cancer xenografts which retain stable prostate cancer cell phenotypes through multiple passages in SCID mice. Various embodiments are provided, including androgen dependent and androgen independent xenografts, xenografts which express prostate specific antigen (PSA) at clinically reflective levels, xenografts which express wild-type androgen receptor (AR) and xenografts which exhibit chromosomal abnormalities. Still other embodiments include xenografts which retain all of the foregoing characteristics as well as xenografts that model the progression to androgen independent disease. These and other embodiments of the invention are described in more detail by way of the examples which follow. As described in Example 1, a number of subcutaneous xenografts were successfully established from tumor tissue explants taken from the prostate gland and from bone, lymph, and lung metastases of patients with stage C or D prostate cancer. These xenografts grow and passage in SCID mice with high frequency and retain definitive characteristics of human prostate cancer, even in late passages. One xenograft, designated LAPC-4, has been adapted to tissue culture as a stable cell line and has been in continuous culture for 18 months.

Xenografts such as the LAPC-4 xenograft described in Example 1 are of particular interest. Similar to prostate tumors isolated directly from patients, LAPC-4 cells retain expression of prostate specific antigen (PSA), androgen receptor (AR), and prostatic acid phosphatase through more than 20 passages. Moreover, the LAPC-4 xenograft is unique among prostate cancer model systems since its AR contains no mutations in the DNA or ligand binding domains and AR expression is retained in androgen independent LAPC-4 sublines. In addition, the LAPC-4 xenograft models the transition from androgen-dependent to androgen-independent disease as well as the development of micrometastatic disease. For example, LAPC-4 tumors passaged in male mice retain androgen-dependent growth characteristics, whereas tumors passaged in castrated males or female mice acquire a stable androgen-independent phenotype. These sublines can be easily expanded using the methods of the invention to provide ample tissue for molecular and biochemical analysis of events associated with androgen-independent growth. There are few other experimental models for androgen-dependent prostate cancer growth. Published reports include the widely used LNCaP cell line (Lim et al., 1993; Gleave et al., 1992) and two recently described xenografts, CWR22 (Weinstein et al., 1994) and LuCaP23 (Lin et al., 1996). The LAPC-4 xenograft is unique because tumors placed under the selective pressure of androgen deprivation reproducibly evolve to an androgen-independent state, providing an opportunity to evaluate the molecular changes associated with androgen-independence over time and directly test their functional importance.

This aspect of the invention also provides assays for determining the function or effect of various genes on prostate cancer cells. In one embodiment, the assay comprises isolating prostate cancer cells from a prostate cancer xenograft (e.g., subcutaneous, intraprostatic), transducing the cells with the gene of interest such that the transduced cells express or overexpress the gene, establishing a subcutaneous or intraprostatic xenograft tumor in a SCID or other immune deficient mouse with the transduced cells and evaluating the growth of the resulting xenograft. The effect of expressing the gene on the growth of the xenograft may be determined by reference to a control xenograft established with untransduced prostate cancer cells, preferably isolated from the same parental xenograft. In another embodiment, the assay comprises generating a prostate cancer xenograft (e.g., subcutaneous, intraprostatic), transducing the cells of the xenograft with the gene of interest in vivo, and evaluating the growth of the xenograft, wherein the effect of the gene on the growth of the xenograft may be determined by reference to a control xenograft.

Similarly, the invention provides assays for determining the effect of candidate therapeutic compositions or treatments on the growth of prostate cancer cells. In one embodiment, the assay comprises applying the composition or treatment to a SCID or other immune deficient mouse bearing a subcutaneous human prostate cancer xenograft and determining the effect of the treatment on the growth of the xenograft. In another embodiment, a SCID or other immune deficient mouse bearing an intraprostatic xenograft is used to determine the effect of the composition or treatment.

This aspect of the invention may also have various clinical applications, including using the model in a method to assess prognosis of a patient with locally advanced or metastatic prostate cancer. For example, in one embodiment, the method comprises implanting a prostate tumor sample from the patient into an immune deficient mouse subcutaneously, and allowing the implanted sample to grow as a xenograft in the mouse. The rates of xenograft growth may be used as a prognostic indicator. The results of such analysis may assist a treating oncologist in determining how aggressively to treat a patient.

Models that Simulate Prostate Cancer Micrometastasis

Another aspect of the invention provides models and methods for simulating and studying the process of micrometastasis in human prostate cancer. SCID mice bearing subcutaneous prostate cancer xenografts show evidence of circulating prostate cancer cells. Thus, this model duplicates the process of cell migration from the primary tumor to the bone marrow and other distant sites of micrometastasis. As detailed in Example 3, 100% of male mice inoculated subcutaneously with xenograft LAPC-4 cells developed localized subcutaneous tumors within 4 to 6 weeks without evidence of bony metastasis. However, when these animals were examined for the presence of micrometastatic disease, up to 50% of the mice had detectable prostate cancer cells in bone marrow and blood. Using the same semi-quantitative RT-PCR assay that has been applied to large surveys of prostate cancer patients, micrometastatic prostate cancer cells were found at levels comparable to about 0.1 to 1.0% of the total mouse bone marrow. Similar results were obtained by immunohistochemical analysis for PSA expression. Thus, subcutaneous growth of prostate cancer xenografts mimics the clinical observation that prostate cancer cells circulate in the blood and lodge in the bone marrow, even in early stage disease.

In one embodiment, simulating or mimicking prostate cancer micrometastasis comprises establishing a subcutaneous prostate cancer xenograft in a SCID or other immune deficient mouse and allowing the tumor to grow for a time sufficient to permit the detection of prostate cancer cells in the peripheral blood of the mouse. The presence of micrometastasis is monitored by detecting prostate tumor cells which have migrated to the lympahtic and/or vascular system, bone, lung, liver, and/or other sites distant from the primary xenograft site. Detection of such cells may be accomplished by, for example, assaying for the presence of human PSA mRNA in the peripheral blood using an RT-PCR assay for PSA mRNA (such as the assay described in Example 3).

In another embodiment, simulating prostate cancer micrometastasis comprises preparing a single cell suspension of prostate cancer cells from a subcutaneous xenograft tumor grown in a SCID (or other immune deficient) mouse, followed by intraprostatic (orthotopic) injection of the single cell suspension into another SCID (or other immune deficient) mouse. The intraprostatic tumor is allowed to grow for a time sufficient to permit the detection of prostate cancer cells in the peripheral blood of the mouse or in other sites distant from the orthotopic tumor. Single cell suspensions prepared from cultured xenograft cells may also be used for intraprostatic (orthotopic) implantation.

This aspect of the invention also provides a framework for testing the effect of certain variables on the development of micrometastasis. Such variables may include the presence or absence of hormones or other growth-modulating factors in the environment of the tumor, the expression status of various genes within the tumor cells, etc. For example, the rate of micrometasis of androgen dependent and androgen independent xenograft variants may be evaluated. Such an evaluation is described in Example 3, using the androgen dependent and independent sublines of the LAPC-4 xenograft, demonstrating a significantly higher rate of micrometastasis in mice bearing the androgen independent LAPC-4 xenografts.

In this regard, the invention provides assays for determining the function or effect of various genes on the progression of prostate cancer micrometastasis. In one embodiment, the assay comprises isolating prostate cancer cells from a prostate cancer xenograft (e.g., subcutaneous, intraprostatic), transducing the cells with the gene of interest such that the transduced cells express or over-express the gene, using the transduced cells to establish a subcutaneous or intraprostatic xenograft tumor in a SCID or other immune deficient mouse, and evaluating the presence and levels of micrometastatic disease by detecting prostate cancer cells in blood, bone marrow, lymph nodes, and/or other sites distant from the site of the primary xenograft tumor. The effect of expressing the gene on the rate of micrometastasis may be determined by reference to a control xenograft established with untransduced prostate cancer cells, preferably isolated from the same parental xenograft. In another embodiment, the assay comprises generating a prostate cancer xenograft (e.g., subcutaneous, intraprostatic), transducing the cells of the xenograft with the gene of interest in vivo, and evaluating the presence and levels of micrometastatic disease, wherein the effect of expressing the gene on the rate of micrometastasis may be determined by reference to a control xenograft.

Similarly, the invention provides assays for determining the effect of candidate therapeutic compositions or treatments on the progression to micrometastatic disease. In one embodiment, the assay comprises applying the composition or treatment to a SCID mouse bearing a subcutaneous human prostate cancer xenograft, and determining the effect of the treatment on micrometastasis by monitoring the presence and levels of prostate cancer cells in the peripheral blood, lymph nodes, bone marrow, and/or other sites distant from the xenograft. In another embodiment, a SCID or other immune deficient mouse bearing an intraprostatic xenograft is used to determine the effect of the treatment on micrometastasis.

This aspect of the invention may also have various clinical applications, including using the model in a method to assess prognosis of a patient with locally advanced or metastatic prostate cancer. For example, in one embodiment, the method comprises implanting a prostate tumor sample from the patient into an immunocompromised mouse subcutaneously and allowing the implanted sample to grow as a xenograft in the mouse. The rates of xenograft growth and the development of micrometastasis may be used as prognostic indicators. The results of such analysis may assist a treating oncologist in determining how aggressively to treat a patient.

Models that Simulate Metastatic Prostate Cancer

Another aspect of the invention provides models and methods for mimicking and studying the development of macrometastatic osteoblastic bone lesions (bone metastasis) in prostate cancer. Subcutaneous growth of xenograft tumors results in detectable micrometastasis, indicating that cells from xenograft tumors in SCID mice have the ability to exit the site of primary tumor growth, circulate in blood, and lodge in the bone marrow, reflecting the human clinical situation.

In one embodiment, simulating the development of prostate cancer bone metastasis comprises injecting a single cell suspension of prostate cancer cells prepared from a subcutaneous prostate cancer xenograft growing in SCID (or other immune deficient) mouse into the prostate of another SCID (or other immune deficient) mouse host, and allowing the resulting orthotopic tumor to grow for a time sufficient to permit the detection of bone metastasis in the mouse. Alternatively, subcutaneous prostate cancer xerografts may be established with such single cell preparations and allowed to grow. Detection of bone metastasis may be accomplished by various means, including histologically, immunohistochemically, and radiographically.

Subcutaneous and orthotopic tumors typically grow quickly, reaching a size which demands that the host animal be sacrificed within about 4–6 weeks. Therefore, alternative methods which increase the number of prostate cancer cells in the bone marrow, thereby obviating this limitation, are also provided. In one embodiment, a single cell suspension prepared from xenograft tumor cells, or from xenograft cells in tissue culture, is injected directly into the bone marrow cavity (e.g., tibial) of a SCID or other immune deficient mouse. The development of micrometastasis, bone tumor growth, and osteoblastic activity may be monitored in various ways, including by immuno-histochemistry and in situ hybridization of bone sections or by radiographic imaging.

As described in Example 6, a single cell suspension of 10,000 xenograft tumor cells prepared from a subcutaneous tumor was injected into the tibia of a SCID mouse. A small subset of the injected cells was detectable at 2 weeks, followed by small foci of bone tumor growth in a few isolated areas at 4 weeks, followed by extensive macroscopic bone tumor growth, destruction of bone cortex, and net new bone formation by 6–8 weeks. Accordingly, cells isolated from the human prostate cancer xenografts of the invention are capable of proliferation in the microenvironment of the SCID mouse bone marrow cavity.

The foregoing method provides an excellent model for simulating the formation of osteoblastic bone lesions and the progression to this stage of the disease. The model may be used not only to study the molecular and cellular events involved in the progression of this stage of prostate cancer, but also to test the effect of various candidate therapeutic genes, proteins and other compounds. In addition, the model may be used as an assay for assessing the metastatic and osteoblastic potential of prostate cancer cells obtained from human patients.

Accordingly, the invention also provides assays for determining the function or effect of various genes on the progression of prostate cancer bone metastasis. In one embodiment, the assay comprises isolating prostate cancer cells from a prostate cancer xenograft (e.g., subcutaneous, intraprostatic, bone), transducing the cells with the gene of interest such that the transduced cells express or overexpress the gene, introducing the transduced cells into the bone marrow cavity of a SCID or other immune deficient mouse, and monitoring the bone marrow for the presence and levels of osteoblastic macrometastatic lesions. The effect of expressing the gene on the development and growth of bone metastasis may be determined by reference to a control animal receiving untransduced prostate cancer cells, preferably isolated from the same parental xenograft. In another embodiment, the assay comprises generating a bone marrow xenograft in a SCID (or other immune deficient) mouse by injecting a single cell suspension of prostate cancer cells prepared from a subcutaneous or intraprostatic xenograft established in another SCID (or other immune deficient )mouse, transducing the cells of the bone marrow xenograft with the gene of interest in vivo, and evaluating the effect of the gene on the presence and levels of osteoblastic macrometastatic lesions.

Further, the invention provides assays for determining the effect of candidate therapeutic compositions or treatments on the progression of prostate cancer bone metastasis. In one embodiment, the assay comprises applying the composition or treatment to a SCID or other immune deficient mouse receiving an intratibial injection of prostate cancer xenograft cells and determining the effect of the treatment on the progression of bone metastasis by monitoring the tibial bone marrow for the presence and levels of prostate cancer cells and/or osteoblastic macrometastatic lesions. The presence of prostate cancer cells in bone marrow may be detected by various means, including histologically, immunochemically, or by assaying for the presence of PSA mRNA or protein. The presence of osteoblastic macrometastatic lesions may be detected using histologic, radiographic, or other imaging techniques.

This aspect of the invention may also have various clinical applications, including using the model in a method to assess the prognosis of a patient with locally advanced prostate cancer, and in particular, to predict the likelihood that a patient will progress to metastatic disease. For example, in one embodiment, the method comprises injecting a single cell suspension prepared from a patient's prostate biopsy material directly into the bone marrow of an immune deficient mouse and then monitoring the bone marrow for the development of bone lesions. The rate of bone lesion growth and osteoblastic activity may be used as prognostic indicators. The results of such analysis may assist a treating oncologist in determining how aggressively to treat a patient with locally advanced disease.

Similarly, the effect of various therapeutic strategies for managing locally advanced or metastatic disease in a particular patient may be predicted. For example, the effect of a treatment strategy may be predicted by applying the treatment to an immune deficient mouse receiving a bone marrow injection of the patient's prostate cancer cells The effect of the treatment may be monitored by comparing the rate and extent of bone lesion growth and osteoblastic activity in the test mouse to the corresponding rates in an untreated control mouse receiving a corresponding bone marrow injection. In addition, this method may be used to test the effectiveness of a treatment strategy on androgen independent prostate cancer cells by using a female or castrated male immune deficient mouse in order to select for androgen independent clones in the patient's tumor material. The results of such tests may assist a treating oncologist in determining which of several alternative therapies should be used to manage a particular patient's disease.

Short-term Culture of Xenograft Tumor Cells

Xenograft tumor cells may be expanded using short-term in vitro tissue culture techniques well known in the art. In addition, different clonal populations from a xenograft tumor may be isolated through tissue culture techniques. In this regard, the invention provides methods for preparing single cell suspensions from xenograft tumor tissue samples. In one embodiment, xenograft tumor tissue is surgically removed from a subcutaneous xenograft tumor, disaggregated, and proteolytically digested, using the method described in Example 2 or similar methods. Cells may then suspended in a solution of Matrigel, other basement membrane compositions, saline, or other buffers. Such preparations are useful for establishing new tumors in SCID or other immune deficient recipient mice by, for example, subcutaneous inoculation, intraprostatic injection, or by injection directly into bone marrow metaphyses. Cell suspensions may be prepared from subcutaneous, intraprostatic, bone or other orthotopic tumors growing in SCID or other immune deficient mice.

Methods of Expanding and Purifying Prostate Cancer Cell Populations

Another aspect of the invention provides methods for expanding advanced stage prostate cancer cells, methods for preparing relatively pure populations of prostate cancer cells from heterogeneous populations of cells, and methods for propagating stage-specific prostate cancer cells in vivo or in vitro. Primary tumor samples are heterogeneous in their cellular compositions, and are usually contaminated with normal and stromal cells. Moreover, it is difficult to obtain substantial populations of prostate cancer cells from human tissue biopsy material. In contrast, cells harvested from subcutaneous prostate tumors growing in SCID mice predominantly comprise prostate cancer cells. Thus, the models of the invention provide a vehicle for purifying advanced stage human prostate cancer cells from heterogeneous biopsy material.

Serial passage of xenograft tumors in additional mice may be used to further enhance the prostate cancer specificity of the xenograft cellular composition. Similarly, the ability to serially propagate, such as by serial propagation, relatively pure human prostate cancer cells in immune deficient mice provides a means for obtaining large quantities of defined prostate cancer cells.

In one embodiment, tissue harvested from xenograft tumors is enriched for prostate cancer cells by subsequent passage in additional SCID or other immune deficient mice. In another embodiment, cells from xenograft tumors may be cultured in vitro. In another embodiment, single cell suspensions of prostate cancer cells may be prepared from such cultured cells or directly from xenograft tumor tissue. Single cell suspensions prepared from protease digested subcutaneous xenograft tumors retain the biological properties of the parental tumors. The single cell suspensions may be used to establish, for example, new subcutaneous tumors, intraprostatic tumors, or bone tumors. As shown by the experiments set forth in Example 2, as few as 10 xenograft cells can seed a new subcutaneous tumor.

Selective factors may be added to the environment in which the tumor cell enrichment is being conducted in order to expand cells with a particular phenotype. For example, the presence of androgen in the in vivo environment may be controlled by chemical or surgical castration methods well known in the art in order to select for androgen dependent or independent prostate cancer cells. Alternatively, female mice may be used to expand androgen independent cells. Similarly, in an in vitro environment, the absence of androgen in growth media may be used to select androgen independent prostate cancer cells.

In addition, the presence of cell surface proteins on the tumor cells of subcutaneous xenografts may be used to distinguish and isolate human prostate cancer cells from other cells. In particular, antibodies to cell surface proteins differentially expressed on prostate cancer cells (relative to their expression on murine marrow cells) may be used to isolate prostate cancer cells from xenograft tumor tissue, from cells in culture, etc., using antibody-based cell sorting or affinity purification techniques. Most preferred for antibody-based cell sorting are antibodies to cell surface proteins which are human prostate cancer specific. However, antibodies to other human proteins may be effectively employed provided they do not exhibit significant cross-reactivity with the murine homolog of the protein. An examples of such a protein is human galectin-6.

The ability to generate large quantities of relatively pure advanced stage human prostate cancer cells which can be grown in tissue culture or as xenograft tumors in SCID or other immune deficient mice provides many advantages, including, for example, permitting the evaluation of various transgenes or candidate therapeutic compounds on the growth or other phenotypic characteristics of a relatively homogeneous population of prostate cancer cells. Additionally, this feature of the invention also permits the isolation of highly enriched preparations of human prostate cancer specific nucleic acids in quantities sufficient for various molecular manipulations. For example, large quantities of such nucleic acid preparations will assist in the identification of rare genes with biological relevance to prostate cancer disease progression.

Another valuable application of this aspect of the invention is the ability to analyze and experiment with relatively pure preparations of viable prostate tumor cells cloned from individual patients with locally advanced or metastatic disease. In this way, for example, an individual patient's prostate cancer cells may be expanded from a limited biopsy sample and then tested for the presence of diagnostic and prognostic genes, proteins, chromosomal aberrations, gene expression profiles, or other relevant genotypic and phenotypic characteristics, without the potentially confounding variable of contaminating cells. In addition, such cells may be evaluated for neoplastic aggressiveness and metastatic potential in the subcutaneous, orthotopic, and bone tumor models of the invention. This aspect of the invention provides a means for testing alternative treatment modalities with a view towards customizing optimal, patient-specific treatment regimens. Similarly, patient-specific prostate cancer vaccines and cellular immunotherapeutics may be created from such cell preparations.

The prostate cancer models of the invention further provide methods for isolating stage-specific prostate cancer cells, including micrometastatic and osteoblastic prostate cancer cells. In one embodiment, micrometastatic cells are isolated from hematopoetic tissues such as bone marrow or blood using antibody-based cell sorting or affinity purification techniques. In another embodiment, osteoblastic prostate cancer cells are isolated from the bone marrow of SCID or other immune deficient mice bearing osteoblastic bone lesions. The presence of such bone lesions may be detected histologically, immunohistochemically, or radiographically. Stage-specific prostate cancer cells may be further expanded and purified by subsequent reimplantation into SCID or other immune deficient mice. For example, osteoblastic prostate cancer cells may be subpassaged in vivo by reinjection into bone marrow or in vitro using defined bone stroma as a growth substrate.

As shown by the experimental work presented in Example 3, small numbers of micrometastatic prostate cancer cells can be detected in and isolated from the bone marrow of SCID mice bearing subcutaneous prostate cancer xenografts. Although these prostate cancer cells represent less than about 1% of the cells in the bone marrow of the host mice, they may be isolated and expanded using cell purification methods, such as those discussed above. In one embodiment, bone marrow harvested from mice bearing subcutaneous xenografts is incubated with a human specific monoclonal antibody to galectin-6 and a secondary antibody conjugated to magnetic beads. Prostate cancer cells are then isolated using Miltenyi Magnetic Minimacs columns (Sunnyvale, Calif.) to magnetically retain antibody-positive cells in the column while allowing antibody-negative cells to pass to the flow-through. Small numbers of micrometastatic prostate cancer cells isolated in this manner may be expanded in vivo by subcutaneous inoculation of Matrigel suspended cells into SCID or other immune deficient mice. Osteoblastic prostate cancer cells may be similarly isolated directly from bone marrow lesions.

The ability to purify and expand stage-specific prostate cancer cells may have various clinical applications. For example, stage-specific prostate cancer cells within clinical material may be isolated by using cell sorting or purification techniques and then expanded as subcutaneous, intraprostatic, or bone tumors in SCID or other immune deficient mice, depending on the particular objective. In one embodiment, micrometastasis are isolated from patient serum, formulated into single cell suspensions, and injected into subcutaneously with the objective of expanding these cells generally. In an alternative embodiment, the micrometastatic cell preparation is injected into the bone marrow of a SCID or other immune deficient mouse with the objective of selectively expanding those cells with osteoblastic characteristic. Prostate cancer cells passaged in this manner may become conditioned by various factors within the microenvironment of the bone marrow and may form osteoblastic lesions which may then be harvested for further use or analysis.

Continuous Cell Lines

The invention also provides continuous human prostate cancer cell lines established by culturing xenograft cell preparations. In one embodiment, the cell line comprises human prostatic cancer cells cultured from a subcutaneous xenograft. In a specific embodiment described by way of Example 9, the cell line LAPC-4 was established by culturing a single cell suspension prepared from the LAPC-4 xenograft. The LAPC-4 cell line expresses PSA, androgen receptor (AR), and is androgen dependent. The LAPC-4 cell line has been growing in continuous culture for 1.5 years, and retains phenotypic characteristics which correlate to the human clinical situation more closely than any other available human prostate cancer cell line.

The cell lines of the invention may be used for a number of purposes. By way of example and not by way of limitation, the cell lines may be used as a source of large quantities nucleic acids and proteins, as a tool for screening and evaluating candidate therapeutic transgenes, proteins and compounds, and as a tool for identifying and isolating prostate specific or differentially expressed genes. Genes which may regulate the growth of prostate cancer can be evaluated by overexpression in transduced cells grown in vitro or in vivo. The effects of genes on micrometastasis and the development of osteoblastic bone lesions may be evaluated in vivo by subcutaneous, intraprostatic, or intratibial inoculation of transduced cells.

EXAMPLES

The invention is further described and illustrated by way of the following examples and the experimental details therein. This section is set forth as an aid to understanding the invention, but is not intended to, nor should it be construed as, limiting the invention as claimed.

Example 1

Generation of Subcutaneous Human Prostate Cancer Xenografts that Simulate Prostate Cancer Progression Materials and Methods Patients: All clinical material was obtained from patients with locally advanced or metastatic (stage C or D) after obtaining informed consent according to an IRB approved protocol. Most patients had undergone some form of androgen ablation therapy (medical or surgical) and shown progressive disease at the time the tissue samples were obtained.

Animals: C.B.17 scid/scid (SCID) mice were bred at UCLA under sterile conditions as previously described (Aldrovandi et al., *Nature* 363:732–736 (1993)). Biopsy material obtained at the time of surgery was placed on ice and immediately transferred to the SCID mouse facility for implantation. A scalpel was used to mince the tissue into 2–3 mm$^3$ sections which were then implanted subcutaneously into the flanks of SCID mice. Mice were anesthetized with methoxyflurane before implantation. Initial implants were performed with 100–200 μl of Matrigel (Collaborative Research, Bedford, Mass.) injected around the implant. Matrigel is an extracellular matrix preparation useful for enhancing the growth of epithelial tumors in vivo (Pretlow (1993), supra; Noel et al., *Biochemical Pharmacology* 43:1263–1267 (1992) and Lim et al., *Prostate* 22:109–118 (1993)). Once a xenograft was passaged 2–3 times, Matrigel was no longer used for serial propagation. Androgen ablation was performed by surgical castration under anesthesia. Tumor sizes were determined by weekly caliper measurements of height, width and depth. Sustained-release testosterone pellets (Innovative Research of America, Sarasota, Fla.) were implanted subcutaneously, as recommended by the manufacturer, in some experiments. Xenografts were stored viably in liquid nitrogen by freezing 1–2mm$^3$ minced tissue sections in DMSO-containing medium.

PCR Assays, Histology and Immunochemistry: DNA from tumor tissue was prepared using SDS detergent extraction and proteinase K digestion as described by Sambrook et al., *Molecular Cloning: A Laboratory Manual,* Cold Spring Harbor Laboratory Press, Edition 2 (1989). RNA was prepared by using a commercially available kit containing guanidine thiocyanate and β-mercaptoethanol (RNAgents Total RNA Isolation System, Promega). To avoid contamination of gross tissue preparations, the tissue homogenizer and all surgical instruments used at the time of necropsy were cleaned by repeated rinses in HCl, DEPC treated water and ethanol. DNA-PCR assays for human β-globin (Aldrovandi et al., supra and Saiki et al., *Science* 230:1350–1354 (1985)) and RT-PCR assays for PSA (Pang et al., *Hum. Gene Ther.* 6:1417–1426 (1995)) were performed as previously described. Briefly, PCR analysis using primers specific for the human β-globin gene were performed for 30 cycles with 100 ng of genomic DNA isolated from the LAPC xenografts. One-tenth of each reaction mixture was analyzed by electrophoresis through agarose gels and visualized by staining for ethidium bromide Murine 3T3 cells were used as a negative control. The quality of all RNA samples was confirmed by ethidium bromide staining for ribosomal RNA and by RT-PCR using primers for β-actin (Pang et al., supra) as a control. Details on the primer sequences can be found in the original references. RT-PCR analysis for PSA expression was performed on 100 ng of total RNA using primers specific for human PSA. The same RNA samples were analyzed using primers which recognize human or murine β-actin to confirm equivalent loading in gels. Immunohistochemical staining for PSA was performed using polyclonal antisera to PSA (Dako) as described (Hsu et al., *Am. J. Clin. Path.* 75:734–738 (1981)).

Sequencing Androgen Receptor DNA: Exons 2–8 of the androgen receptor were sequenced from genomic DNA using intron-specific PCR primers (Marcelli et al., Mol. Endocrinol. 90:1105–1116 (1990)). PCR products were initially screened by SSCP using appropriate positive and negative controls as described (Sutherland et al., J. Urol. 156: 828–831 (1996)). This technique has been shown to detect mutations in prostate cancer clinical specimens even when tumor cells represent only 20% of the population used to make genomic DNA. All SSCP abnormalities were analyzed by sequencing. Two independent DNA samples were analyzed in two independent laboratories to rule out the presence of any mutations.

Cytogenetics: Tumor tissue was aseptically transported in DMEM growth medium supplemented with 10% fetal bovine serum by overnight courier to the University of Utah for cytogenetic preparation and analysis. Briefly, tissue was minced and washed in Hanks Balanced Salt Solution (Ca$^{++}$ and Mg$^{++}$ free), resuspended in RPMI medium supplemented with lot fetal bovine serum, and cells were arrested in metaphase with 0.001 μg/ml colcemid for 16 hours. Cytogenetic harvests were carried out using standard procedures and, following hypotonic (0.075M) KC treatment and 3:1 methanol/acetic acid fixation, slides were prepared and chromosomes G-banded with trypsin/Wrights stain.

Results

Advanced Stage Prostate Cancer Explants Can Be Serially Propagated in SCID Mice:

Biopsies of locally advanced or metastatic tumor tissue were obtained from a total of 15 patients with locally advanced or metastatic (stage C, D1 or D2) prostate cancer who underwent palliative surgical procedures due to complications from disease. Biopsy material was immediately transferred from the surgical suite to the SCID mouse facility. minced into 2–3 mm3 sections and implanted subcutaneously into SCID mice in the presence of Matrigel. Tumor growth was scored positive only if the explant showed a sustained a two- to three-fold increase in size. In addition to histologic studies, two molecular assays were performed on each xenograft to verify the human origin of the tumors. These include a PCR assay on genomic DNA using primers specific for the human β-globin gene and a quantitative RT-PCR assay on RNA from tumors using primers specific for the human PSA gene. The PSA expression assay was also used to verify the prostatic origin of the xenografts.

The results obtained from subcutaneous implantation of tumor tissue samples from two separate series of these 15 patients are individually described below (i.e., the LAPC-1 through LAPC-8 series, and the LAPC-9 through LAPC-15 series).

LAPC-1 through LAPC-8 Series

Explants from six of eight patients (named LAPC 1–8 for Los Angeles Prostate Cancer) formed tumors after a latent period which varied from 2–10 months (Table 1). The six explants which grew were passaged into secondary recipients in an attempt to establish permanent xenografts. Two of these (LAPC-1 and LAPC-5) were terminated after 3–4 passages because we were unable to detect human DNA or expression of PSA in the tumors. These explants perhaps were overgrown by cells of murine origin because they contained human DNA content and expressed PSA during early passages of LAPC-5 (Table 1, column 6,7).

Figure 2:
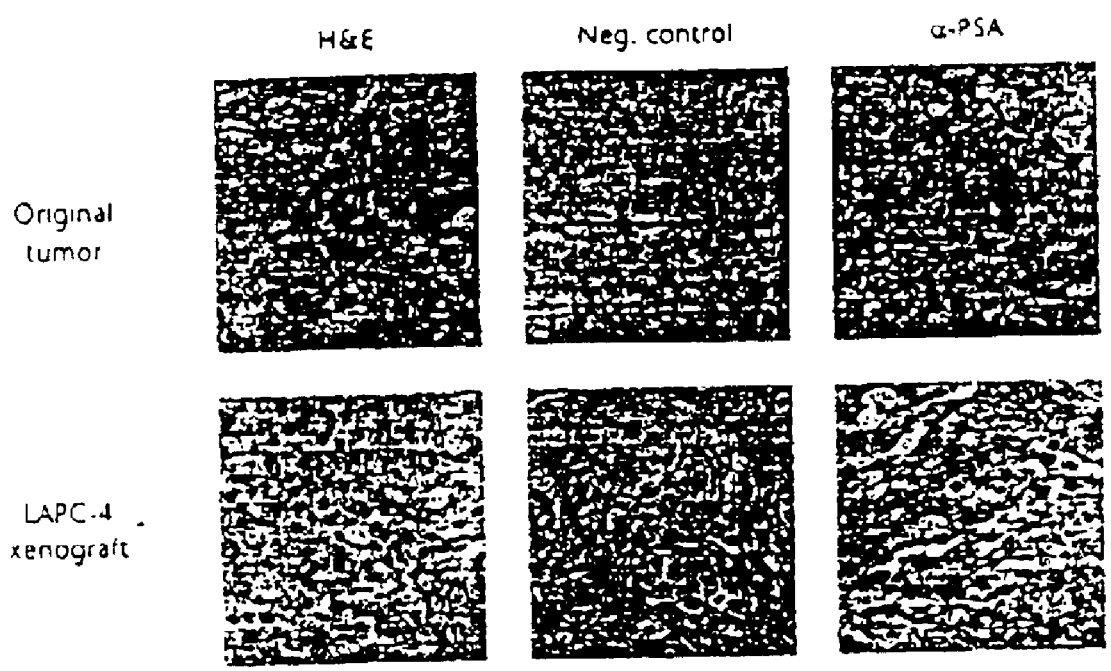
FIG. 2. Photographs of immunohistochemical analysis of the LAPC-4 xenograft, showing expression of PSA. Paraffin sections of formalin-fixed tissue from the original tumor sample obtained at the time of surgery (top row) and the LAPC-4 xenograft (bottom row) were stained with hematoxylin and eosin (left), a control antibody (middle) and an antibody specific for human PSA (right).

The remaining four explants (LAPC-3,4,7 and 8) were successfully propagated as subcutaneous xenografts in secondary recipients for between 4 and 20 (or more) passages. RT-PCR was used to measure the levels of PSA mRNA expression in comparison with LNCaP, a prostate cancer cell line known to express PSA mRNA and protein. This assay is semi-quantitative and is capable of detecting PSA mRNA expression from 100 LNCaP cells diluted into $10^5$ mouse cells (1 in 1000 or 0.1%) (FIG. 1B, top panel). Four of the six xenografts (LAPC-3, 4, 5, 8) expressed human PSA at levels that varied from 1% to 100% of the level found in LNCaP cells (FIG. 1B, top panel). Simultaneous RT-PCR analysis using primers for $\beta$-actin confirmed that equivalent levels of RNA were present in each reaction (FIG. 1B, bottom panel). FIG. 2 shows a histological comparison of the original LAPC-4 tumor sample obtained, at the time of surgery to the same tumor after passage as a xenograft in male mice. The hematoxylin and eosin stained sections (FIG. 2, left panels) show a monotonous population of anaplastic cells which stain positive for PSA using immunohistochemical analysis (FIG. 2, right panels). These findings demonstrate that advanced stage prostate cancer explants can be serially propagated in SCID mice and retain definitive tissue specific gene expression.

TABLE 1

SUMMARY OF IMPLANTS INTO SCID MICE/LAPC-1 THROUGH LAPC-8 SERIES[1]

| Patient Implant (disease stage) | Biopsy site | Growth | Time interval for tumor growth | Passages | Human DNA Status[2] | PSA Status[3] | Notes |
|---|---|---|---|---|---|---|---|
| LAPC-1 (stage D) | liver met | yes | 2 months | 5 | negative on passage | negative | overgrowth by tumor of murine origin after serial passage |
| LAPC-2 (stage D) | lymph node met | no | no growth at 2 years | 1 | — | — | — |
| LAPC-3 (stage D) | prostate-channel TURP | yes | 10 months | 3 | positive | positive | no PSA positive cells outside site of implantation (n = 2) |
| LAPC-4 (stage D) | lymph node met | yes | 3 months | >8 | positive | positive | PSA positive cells in bone marrow, spleen, blood in 50% of mice (n = 12) |
| LAPC-5 (stage D) | lymph node met | yes | 9 months | 5 | positive, then negative on passage 4 | positive, then negative on passage 4 | overgrowth by tumor of murine origin on passage 4 |
| LAPC-6 (stage C) | prostate | no | no growth at 9 months | 1 | — | — | — |
| LAPC-7 (stage C) | prostate | yes | 3 months | 2 | positive | negative | — |
| LAPC-8 (stage C) | lymph node met | yes | 10 months | 2 | positive | positive | no PSA positive cells outside implantation site (n = 1) |

[1]locally advanced (stage C) or metastatic (stage D) disease;
[2]determined by PCR of genomic DNA for human $\beta$-globin;
[3]determined by RT-PCR and/or immunohistochemistry Two of the xenografts in this series, LAPC-3 and LAPC-4, have retained constant histologic and molecular features of prostate cancer for more than 6 and 8 passages, respectively. Both xenografts can be frozen viably as tumor explants and recovered from freezing with nearly 100% efficiency. A cell line from the LAPC-4 xenograft was established by serial passage of trypsinized, minced xenograft tissue in Iscove's growth medium supplemented with 20% fetal calf serum. The LAPC-4 cell line has remained established for more than 20 passages and has been in continuous culture for over 18 months. These cells continue to express PSA, form tumors in SCID mice, and retain androgen-responsiveness.

LAPC-9 through LAPC-15 Series

A second series of xenograft experiments was conducted by implanting tissue samples from an additional seven prostate cancer patients with advanced stage (C or D) disease (Table 2). Four of these seven implants have resulted in the generation of androgen-responsive xenografts which express PSA and which are capable of being propagated serially in additional mice (LAPC-9, 12, 14, 15). The LAPC-9 xenograft, generated from a bone tumor biopsy of a patient with hormone-refractory metastatic disease, demonstrates an extremely androgen-sensitive phenotype (PSA levels drop to zero after castration) and has been passaged and viably maintained for about 1 year. The LAPC-14 xenograft, generated from a prostate tumor biopsy of a patient with metastatic disease, demonstrates aggressive growth characteristics and exhibits a high degree of androgen-responsiveness (growth is substantially enhanced by the addition of testosterone).

the modal chromosome number of LAPC-3 was 69, which suggests that this line is near-triploid, yet the presence of four copies of many chromosomes raises the possibility of reduction from tetraploid. Both xenografts show previously reported numerical and structural chromosome abnormalities such as loss of Y and 16. In addition, both xenografts contain a deletion at chromosome 12p12, a karyotypic abnormality that has not been previously reported in prostate cancer.

TABLE 3

CYTOGENETIC ANALYSIS OF LAPC-3 AND LAPC-4 XENOGRAFTS

| Xenograft | Passage number at time of analysis (number of independent tumors) | Number of meta-phases analyzed | Modal Chromo-some Number | Karyotype |
|---|---|---|---|---|
| LAPC-3 | passage 2 (1 tumor); passage 3 (2 tumors) | 80 | 69 | 68–81 XXY + add(1)(p22), |

TABLE 2

SUMMARY OF IMPLANTS INTO SCID MICE/LAPC-9 THROUGH LAPC-15 SERIES[1]

| Patient Implant (disease stage) | Biopsy site | Growth | Time interval for tumor growth | Passages | Human DNA Status[2] | PSA Status[3] | Notes |
|---|---|---|---|---|---|---|---|
| LAPC-9 (stage D) | femur tumor | yes | 5 weeks | 5 | positive | positive | patient hormone-refractory androgen dependent |
| LAPC-10 (stage C/D) | prostate (pro-statecomy) | no | — | — | — | — | Gleason 9 |
| LAPC-11 (stage D) | femur tumor | no | — | — | — | — | 1 week post lupron 2 weeks post flutamide |
| LAPC-12 (stage D) | prostate TURP | yes | 13 weeks | 1 | positive | positive | metastatic hormone refractory |
| LAPC-13 (stage C/D) | trans-rectal biopsy | no | — | — | — | — | Gleason 7 |
| LAPC-14 (stage D) | prostate TURP path neg | yes | 4 weeks | 2 | positive | positive | metastatic PSA < 0. 2 lupron treated androgen responsive |
| LAPC-15 (stage D) | prostate TURP | yes | 12 weeks | 1 | positive | positive | metastatic to bone lupron treated casodex treated X 4 mos |

[1]locally advanced (stage C) or metastatic (stage D) disease;
[2]determined by PCR of genomic DNA for human β-globin;
[3]determined by RT-PCR and/or immunohistochemistry LAPC-3 and LAPC-4 Xenografts Contain Chromosome Abnormalities Extensive cytogenetic studies of human prostate cancer have been difficult due to heterogeneity of clinical material obtained at surgery and limited growth of prostate tumor cells in vitro. To determine if passage of prostate tumor tissue in SCID mice might facilitate karyotypic analysis, early passage tumors from the LAPC-3 and LAPC-4 xenografts were analyzed using standard cytogenetic techniques. A high mitotic yield was obtained from tumor samples from both xenografts and all metaphase cells contained human chromosomes. Detailed composite karyotypes are noted in Table 3 The modal chromosome number of LAPC-4 was 89, suggesting a hypotetraploid line, whereas TABLE 3-continued

CYTOGENETIC ANALYSIS OF LAPC-3 AND LAPC-4 XENOGRAFTS

| Xenograft | Passage number at time of analysis (number of independent tumors) | Number of meta-phases analyzed | Modal Chromo-some Number | Karyotype |
|---|---|---|---|---|
| | | | | −2, +3, +4, +5, del(6)(q21)x2, +7, +9, +9, |

TABLE 3-continued

CYTOGENETIC ANALYSIS OF LAPC-3 AND LAPC-4 XENOGRAFTS

| Xenograft | Passage number at time of analysis (number of independent tumors) | Number of meta- phases analyzed | Modal Chromo- some Number | Karyotype |
|---|---|---|---|---|
| LAPC-4 | passage 3 (2 tumors) | 44 | 89 | −11, del(12) (p12), −13, −13, +14, t(14; 14)(q10; q10), −16, +18, +19, +20 [cp80] 76–92, XX, −Y, −Y, add(8) (p23), +9 del(12)(p12), −14, −16, −18, −21, +mar1, +mar2[cp44] |

Progression of LAPC-4 Xenograft to Androgen Independence

Figure 3:
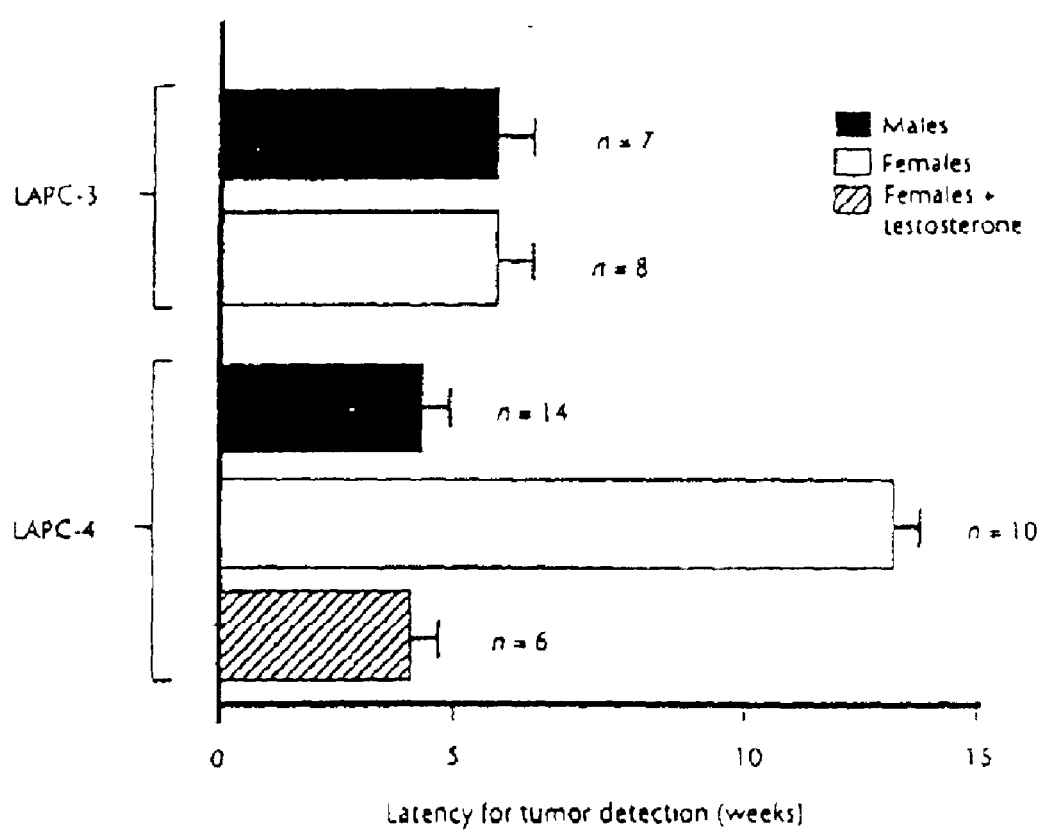
FIG. 3. Bar graphs showing androgen sensitivity of the LAPC-3 and LAPC-4 xenografts in vivo. Equal size implants of the LAPC-3 and LAPC-4 xenografts were passaged simultaneously into male or female mice and examined weekly for the formation of tumors.

Prostate cancer cells are exquisitely sensitive to the growth stimulatory effects of androgen, but androgen-independent disease eventually develops in patients under the selective pressure of androgen deprivation. The mechanism for this transition to androgen-independent growth is unknown. The question of whether this phase of the disease could be modeled in SCID mice was determined using the LAPC-4 xenograft, which reproducibly forms tumors on serial passages in male mice with 100% frequency. The androgen dependence of the xenograft was measured in vivo by comparing the growth rates after implantation in intact male mice with those from castrated male mice or female mice. For LAPC-4, the average time for tumor formation in castrated male mice or female mice (n=10) was 13.4 weeks versus 4.3 weeks in intact males (n=14) (FIG. 3). The delayed growth in female mice was reversed by implantation of a 90-day sustained-release testosterone pellet (FIG. 3). The androgen-independence of tumors growing in female or castrated male mice was confirmed by secondary transfer experiments. Once established, these tumors grew within 4–5 weeks in male, female and castrated male mice.

The LAPC-3 xenograft showed growth characteristics similar to the androgen independent sublines of LAPC-4. After an initial latent period for passage 1, LAPC-3 tumors grew within 7–8 weeks regardless of the hormonal background of the recipient (FIG. 3), clearly establishing this xenograft as androgen independent.

Figure 4:
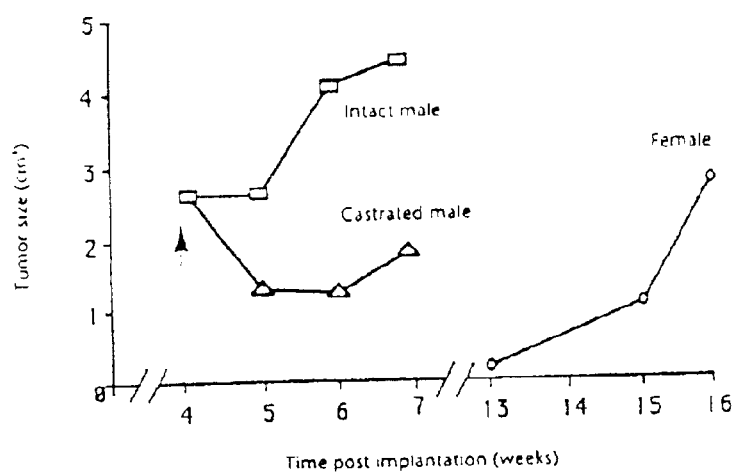
FIG. 4. Regression and regrowth of LAPC-4 tumors following castration.
Figure 4:
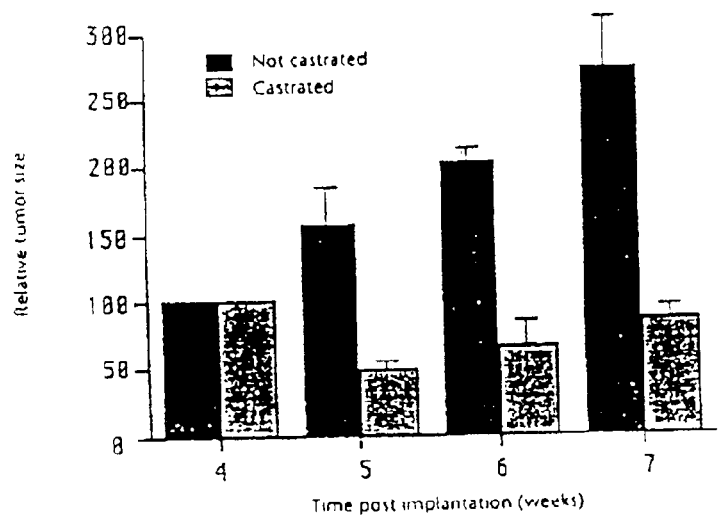

Clinically, anti-androgen therapy causes temporary regression of disease in most patients with advanced prostate cancer. To determine if a similar phenomenon is observed in the mouse model, the effect of acute androgen deprivation on established tumors growing in male mice was examined. Equivalent size implants of the LAPC-4 xenograft were passaged into a cohort of 14 male mice, all of which developed easily measurable tumors after four weeks. Half of these mice underwent castration, then the tumor sizes in each group were determined weekly by caliper measurement of tumor diameters in three dimensions. Tumors in the uncastrated mice doubled in size over a 2–3 week period (FIG. 4). In contrast, the castrated mice showed a decrease in tumor size at one week of approximately 50 percent which persisted for 2–3 weeks. These tumors resumed growth after a variable latent period (3–8 weeks) and eventually grew to the same size seen in uncastrated mice. These results show that the LAPC-4 xenograft displays androgen-dependent growth, that androgen-independent sublines can be developed, and that this xenograft simulates the clinical transition from androgen-sensitive to androgen-independent disease.

LAPC-3 and LAPC-4 Express Wild-type Androgen Receptors

To determine whether similar mutations are present in LAPC-3 and LAPC-4, exons 2–8 of the androgen receptor gene, which span the DNA binding and ligand binding domains of the receptor, were sequenced. Single-strand conformational polymorphism (SSCP) analysis was also performed. Each exon was amplified by PCR from genomic DNA of early and late passage tumors and analyzed using previously characterized mutant and wild-type androgen receptor DNA as positive controls (Sutherland et al., 1996). The results show that both LAPC-3 and LAPC-4 contain wild-type sequences in exons 2–8. Furthermore, these sequences remain wild-type in androgen independent LAPC-4 sublines. Immunoblot analysis confirmed expression of androgen receptor protein of the appropriate size. These results provide definitive evidence that androgen independent prostate cancer progression can occur in the absence of androgen receptor mutations in the DNA or ligand binding domains.

LAPC-4 Cells can be Efficiently Transduced with Retroviruses

LAPC-4 xenograft cells can be successfully transduced by retroviruses packaged transiently in 293T cells with an amphotropic envelope protein. LAPC-4 cells were infected with retrovirus stocks expressing the cell surface Thy-1 protein and expression detected by flow cytometry using an antibody to Thy-1. The results showed Thy-1 expression in up to 50% of the cells 48 hours after infection, indicating successful retroviral-mediated transduction of the Thy-1 gene into LAPC-4 cells.

Example 2

Preparation of Single Cell Suspensions of Xenograft Cells

Materials and Methods

Single cell suspensions of subcutaneous LAPC-4 tumors were prepared as follows. After removing xenograft tissue from SCID mouse, tissue was minced into 1–2 mm³ sections while the tissue was bathed in 1× Iscoves medium, minced tissue was then centrifuged at 1.3K rpm for 4 minutes, the supernatant was resuspended in 10 ml ice cold 1× Iscoves medium and centrifuged at 1.3K rpm for 4 minutes. The pellet was then resuspended in 1× Iscoves with 0.1% pronase E and incubated for 18 minutes at room temperature with mild rocking agitation followed by incubation on ice for 2–4 minutes. The mixture was then filtered using a 200 μm nylon mesh filer. Filtrate was centrifuged at 1.3K rmp for 4 minutes, and the pronase was removed from the aspirated pellet by resuspending in 10 ml Iscoves and re-centrifuging. Resulting pellets were resuspended in PrEGM pre-incubated at 37 degrees C. Cell counts were determined, and limiting dilutions were formulated as indicated in FIG. 5.

Results

Figure 5:
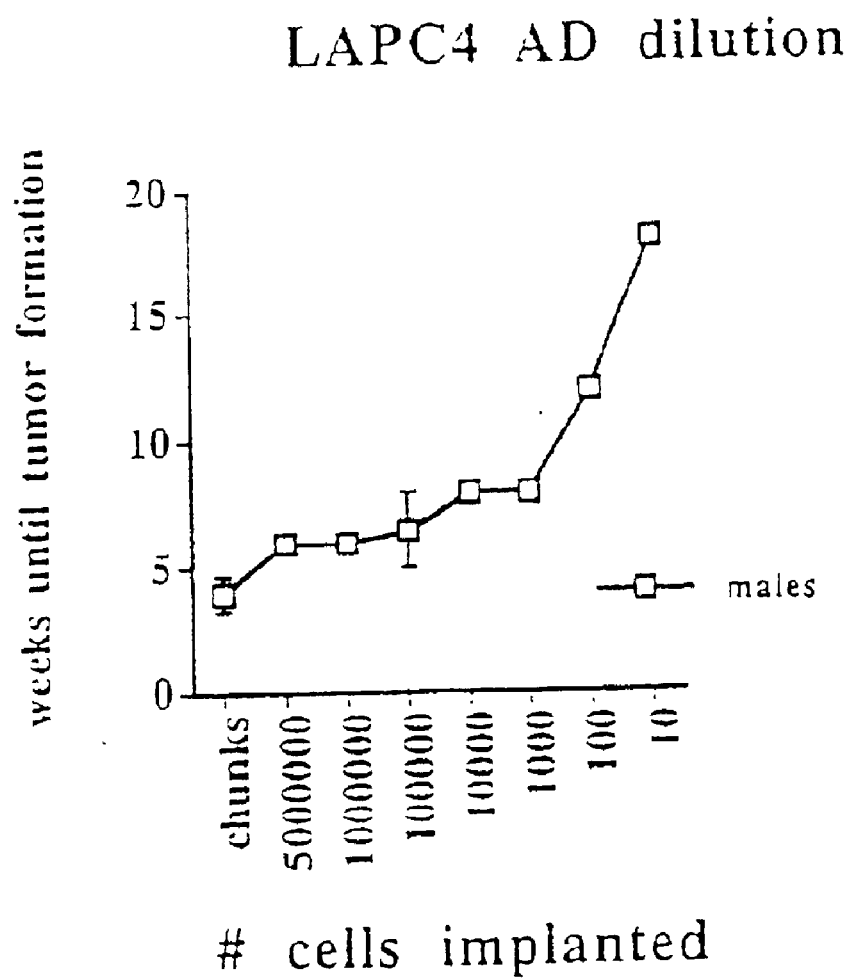
FIG. 5. Line graph showing limiting dilution analysis of LAPC-4 engraftment in male mice.

The results of a limiting dilution analysis of tumor engraftment using single cell suspension of LAPC-4 xenograft cells are shown in (FIG. 5). The results show that single cell suspensions of xenograft cells can form subcutaneous tumors in male mice after injection of as few as 10 LAPC-4 cells and that these cells retain the androgen responsiveness of the parental tumors.

Example 3

Figure 6:
FIG. 6. Photographs showing detection of micrometstatic disease in mice bearing LAPC-4 xenografts. Total RNA was isolated from the murine tissues indicated and analyzed for the expression of PSA (a) or β-actin (b) using RT-PCR. The results from the tumor and various tissues of three representative mice are shown. Tissues from a fourth mouse (control SCID) were analyzed as a negative control. The signal can be quantified by comparison to with LNCaP (lane 1). No RNA was added to the negative control sample (lane 2).

Simulation of Progression to Micrometastasis in SCID Mice Bearing Subcutaneous Tumors Materials and Methods The LAPC-4 xenograft was used in this study. This xenograft was derived from a lymph node containing metastatic prostate cancer cells, and 100% of male mice inoculated subcutaneously with LAPC-4 cells develop localized tumors after 4–6 weeks without evidence of bony metastasis. The presence of micrometastasis in SCID mice implanted with LAPC-4 tumors was determined by analyzing the peripheral blood for prostate cancer cells using RT-PCR assays for PSA mRNA. Simultaneous RNA-PCR studies using β-actin primers demonstrated equivalent RNA loading. To confirm that positive PSA mRNA signals were not due to contamination with tumor cells during the necropsy procedure of during the preparation of RNA, samples were simultaneously prepared from a control mouse that was not implanted with a xenograft. No PSA expression was detected in control mice, even after prolonged autoradiograph exposure times (FIG. 6). Bone marrow, spleen, liver, lung and kidney tissue from mice implanted with subcutaneous LAPC-4 tumors was also analyzed for the presence of prostate cancer cells using RT-PCR to detect PSA mRNA.

Results

Examples of the analysis from two mice (FIG. 6A, mouse nos. 213 and 241) demonstrate detection of PSA mRNA in blood at a 0.1–1.0% level, which is comparable to levels reported in clinical studies. Other organs were positive in several mice, including bone marrow (mouse 213, 241), lung (mouse 214), and spleen (data not shown). The results from 12 animals bearing LAPC-4 xenografts (Table 4) show that 50 percent of mice have PSA mRNA positive cells (level of PSA expression by RT-PCR of 0.1 percent or greater) detected in peripheral blood, bone marrow or spleen. The level of expression was roughly quantitated by comparison to a series of LNCaP cells diluted into murine fibroblasts and varied from 0.1% to 1.0%. It is of interest that the frequency of detecting micrometastatic disease was higher (80%) in female mice or in male mice castrated prior to implantation compared to intact males (27%). These results suggest that the transition to androgen-independent disease is associated with a higher metastatic rate, a hypothesis which is also supported by clinical experience.

TABLE 4

FREQUENCY OF DETECTION OF PSA POSITIVE CELLS IN HEMATOPOETIC TISSUES OF LAPC-4 BEARING SCID MICE

| Group | Number of mice with PSA positive cells in hematopoietic organs per total number analyzed |
|---|---|
| Intact Males | 2/7 (29%) |
| Castrate Males (or Females) | 4/5 (80%) |
| Total | 6/12 (50%) |

Example 4

Generation of Intraprostatic Tumors with Xenograft Cells

Materials and Methods

Single cell suspensions were prepared from subcutaneous xenografts as described in Example 2. SCID mice were anesthetized with Ketamine/Xylazine prior to implantation. Transverse incisions were made in the lower abdomen of mice, abdominal wall muscles were incised, and the bladder and seminal vesicles were delivered through the incision to expose the dorsal prostate. Approximately 10,000 LAPC-4 suspended in 10 μl PrEGM were slowly injected into the dorsal prostate under the capsule via a 30 gauge needle, and the incisions closed using a running suture.

Results

Intraprostatic injection of single cell suspensions prepared from the LAPC-4 and LAPC-9 xenografts and from the LAPC-4 cell line resulted in orthotopic tumors in recipient SCID mice with 100% efficiency.

Example 5

Simulation of Progression to Metastatic Stage of Prostate Cancer in SCID Mice Bearing Intraprostatic Tumors Materials and Methods Single cell suspensions of LAPC-4 xenograft cells were prepared and used to establish orthotopic tumors in the prostates of SCID mice as described in the preceding example. The presence of metastases were determined by histologic examination and by RT-PCR to detect PSA mRNA between 8 and 12 weeks post-injection.

Results

The results, shown in Table 5 below, indicate high frequencies of lymph and pulmonary metastasis as well as a significant frequency of bone marrow metastasis formation. An enhanced frequency of bone metastasis was observed in a subset of the mice pretreated with a combination of radiation and NK cell depletion. Similar results were obtained using the LAPC-9 xenograft.

TABLE 5

PATTERN OF METASTASIS AFTER ORTHOTOPIC INJECTION OF LAPC-4

| TUMOR SITE | FREQUENCY |
|---|---|
| Local Tumor | 100% |
| Pelvic Lymph Nodes | 90% |
| Lung | 90% |
| Bone Marrow | 30% |

Example 6

Simulation of Progression to Osteoblastic Bone Metastasis in SCID Mice Inoculated Intratibially with Single Cell Suspensions of Xenograft Cells Materials and Methods Tibial Injection Assay: Prostate cancer cells were isolated from a subcutaneous xenograft LAPC-4 tumor and prepared as a single cell suspensions as described in Example 2. Ten thousand LAPC-4 cells suspended in 1 μl Matrigel were surgically injected into each proximal tibial metaphyses of a cohort of SCID mice via a 27 gauge needle. Three mice were sacrificed at each of 2, 4, 6, 8 and 12 weeks post injection. Serum PSA levels were periodically assayed by ELISA. At 2 weeks, frozen bone sections were analyzed immunohistochemically for cytokeratin-18 staining with an antibody specific for human cytokeratin-18 or an isotype control antibody. Longitudinal sections of tibias from mice sacrificed at 4, 6 and 8 weeks were analyzed for tumor growth by hematoxylin and eosin (H+E) staining of decalcified paraffin sections. Radiographs of mice were taken at necropsy to monitor evidence of osteoblastic bone lesions.

Results

Figure 7:
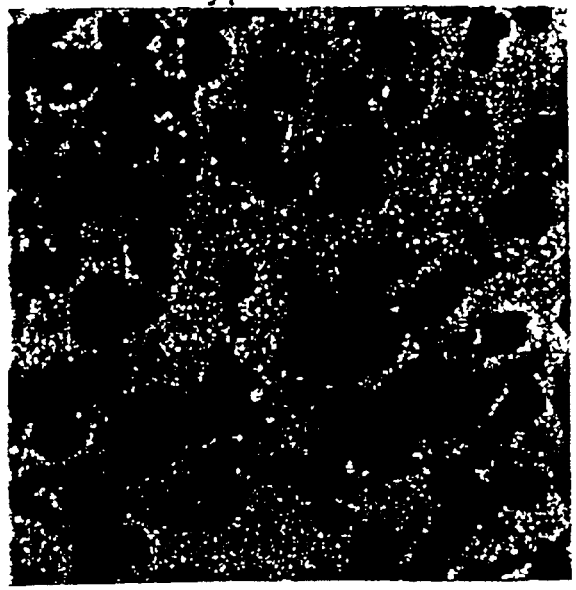
FIG. 7. Photographs showing detection of LAPC-4 cells in bone by immunohistochemistry after 2 weeks. Frozen sections of the tibia of mice injected with LAPC-4 cells were stained with an antibody to cytokeratin-18 (bottom panel) or an isotype control antibody (top panel). The four cells staining red are LAPC-4 cells.
Figure 7:
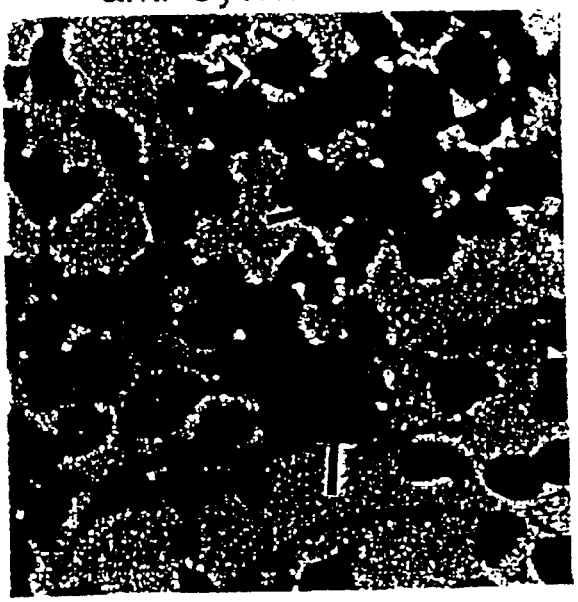

At 2 weeks, small numbers of human prostate cancer cells were visualized by immunohistochemical staining with anti-cytokeratin-18 antibody (FIG. 7). Cytokeratin-18 positive cells were observed scattered throughout the medulary cavity. This data indicates that the majority of LAPC-4 cells injected into the mouse tibia either die or migrate to other locations since only a small subset of the injected cells can be detected at this time point.

Figure 8:
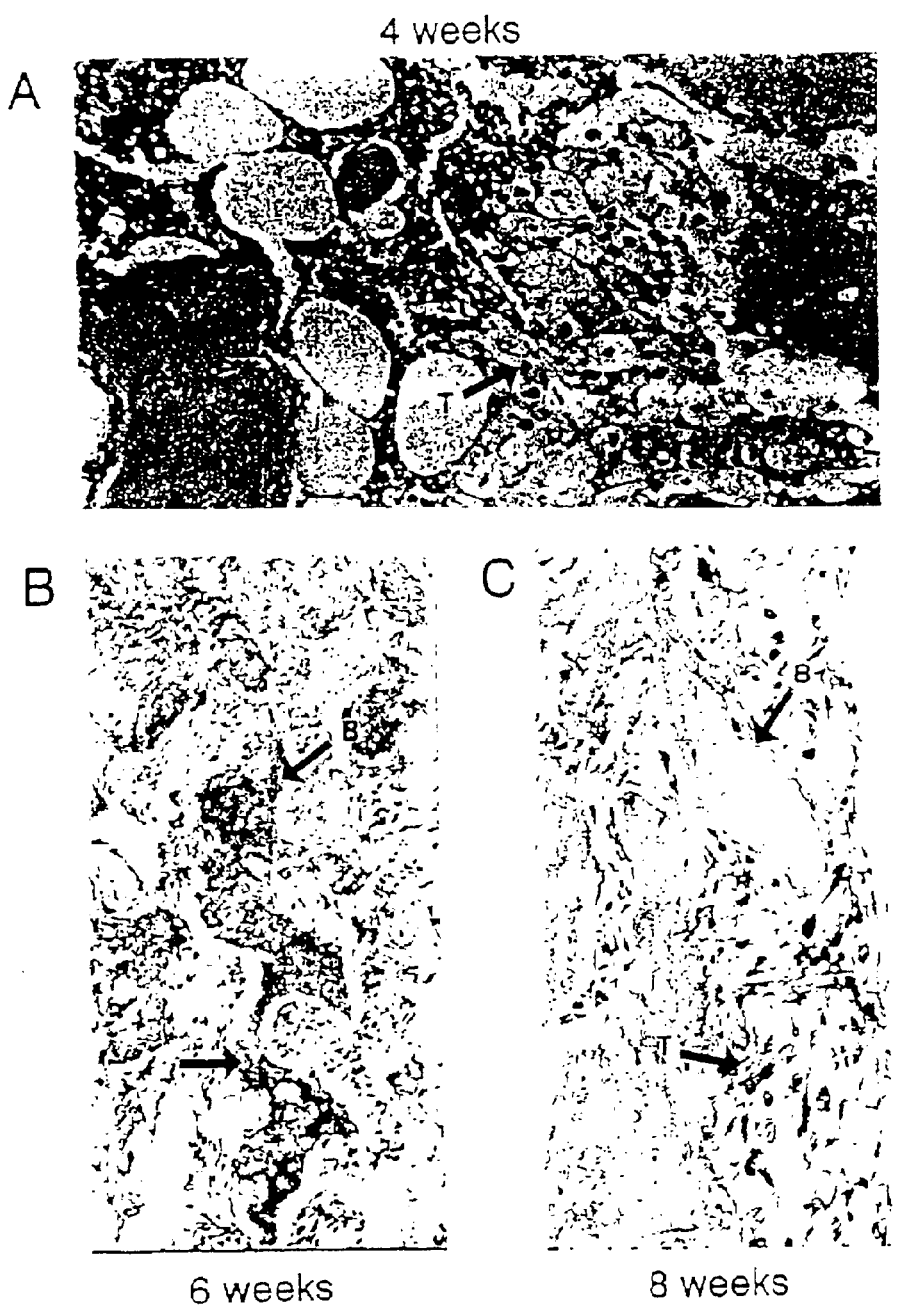
FIG. 8. Photographs showing LAPC-4 causes bone lesions. Hematoxylin and eosin sections of the tibia are shown at 4, 6 and 8 weeks following intratibial injection of LAPC-4 cells. Panel A shows a small focus of tumor formation adjacent to normal bone and hematopoiesis. Panels B and C show progressive increase in new bone formation in response to surrounding tumor cells.

At 4 weeks, small foci of tumor growth were observed in a few isolated areas, usually adjacent to normal bone spicules, by H+E histology (FIG. 8A) and PSA could be detected in serum. At the 6 and 8 week time points, more extensive tumor growth throughout the marrow cavity was observed together with a progressive increase in new bone formation indicative of osteoblastic activity within the marrow cavity in response to surrounding tumor cells (FIG. 8B and C). Serum PSA levels were markedly elevated at this time point.

Figure 9:
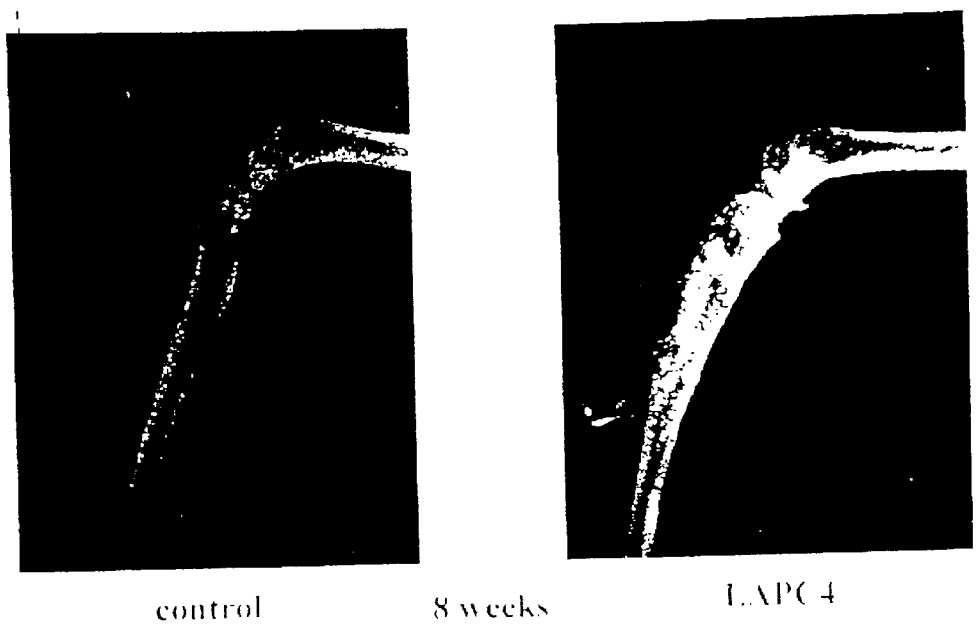
FIG. 9. Radiographic evidence of osteoblastic bone lesions Induced by LAPC-4. X-rays of mice were performed at 8 weeks post injection of LAPC-4 cells in the tibia (right panel). The bone shows evidence of erosion of the cortex with enhanced bone density in the marrow cavity due to osteoblastic activation.

By 8 weeks, bone lesions were visible radiographically as a mixture of osteoblastic and osteolytic lesions with dominant bone formation similar to clinical observations in human prostate cancer. Referring to FIG. 9, the left panel shows a radiograph of a normal mouse tibia with sharp, well defined cortex and relatively radioopaque marrow cavity. The right panel is a radiograph of the marrow cavity of the tibia injected with LAPC-4 xenograft cells, showing a heterogeneous increase in bone density due to osteoblastic activity and destruction of one area of the cortex. These results indicate that LAPC-4 xenograft cells can proliferate in murine bones, suggesting that the crosstalk between bone stroma and prostate cancer cells can occur across species.

Example 7

Figure 10:
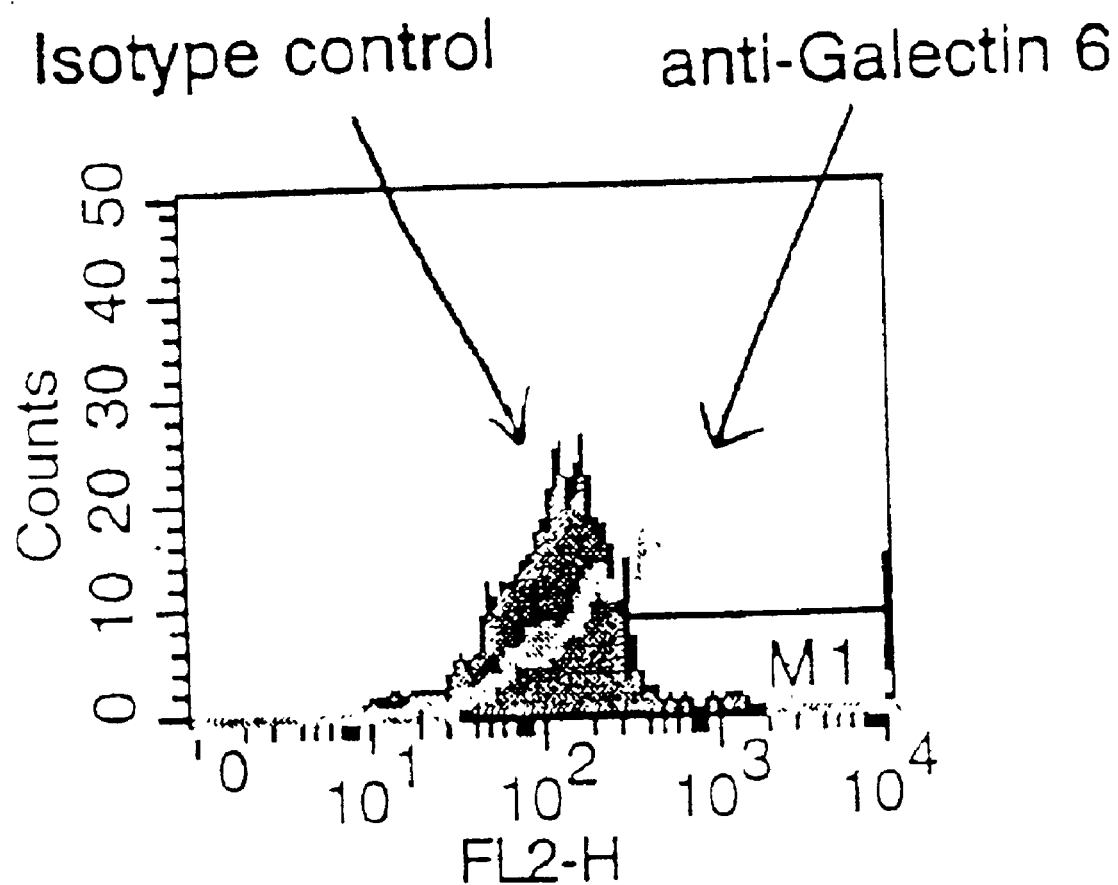
FIG. 10. Flow cytometry analysis of LAPC-4 cells stained with anti-galectin-6 antibody showing the expression level relative to an isotype control antibody.

Isolation of Prostate Cancer Cells from Bone Marrow of SCID Mice Bearing Subcutaneous Xenografts The presence the cell surface protein galectin-6 on LAPC-4 cells was established by incubating intact LAPC-4 cells with a human specific monoclonal antibody to galectin 6 or isotype control. The antibody was visualized by flow cytometry following incubation with a secondary antibody conjugated to FITC. The flow cytometry results show expression of galectin-6 at a level that is at least one order of magnitude above background (FIG. 10). Similar experiments performed on mouse bone marrow showed no galectin staining.

As described in Example 3, small numbers of prostate cancer cells can be detected in the bone marrow of SCID mice bearing subcutaneous xenografts at 4–6 weeks post-inoculation, representing somewhat less than 1% of the cells in the marrow. This population of prostate cancer cells may be isolated from bone marrow using Miltenyl Magnetic Minimacs (Sunnyvale, Calif.) antibody-based affinity purification system and anti-galectin-6 antibody as follows. Twenty mice bearing subcutaneous LAPC-4 tumors are euthanized 4–6 weeks after implantation of xenografts. Bone marrow is harvested from the tibias and femurs by flushing marrow cavities with saline. Marrow is pooled and incubated with a human specific monoclonal antibody to galectin-6 and a secondary antibody conjugated to magnetic beads and run through the Minimacs column as recommended by the manufacturer. LAPC-4 cells will be retained on the column, while mouse bone marrow cells will pass through. Purified LAPC-4 cells may then be harvested from the column and expanded by seeding subcutaneous tumors in SCID mice.

Example 8

Isolation of Prostate Cancer Cells from Bone Marrow of SCID Mice Injected Intratibially with Xenograft Cells Intratibial tumors are established in SCID mice using LAPC-4 cells as described in Example 6. LAPC-4 cells growing in bone marrow are recovered from mice after necropsy at 12 weeks by flushing the tibial marrow cavity with saline and harvesting the cells. At 12 weeks post-injection, about 90% of the recovered cells are prostate tumor cells with some residual murine bone marrow cells. This population of cells may be further purified for prostate cancer cells using a galectin-6 antibody/magnetic affinity purification approach as described in Example 7.

Example 9

LAPC-4 Cell Line Retains Expression of PSA, Androgen Receptor, and Prostatic Acid Phosphatase Through Multiple Passages Materials and Methods A continuous cell line was established from the LAPC-4 xenograft by serial passage of trypsinized, minced xenograft tissue in Iscove's growth medium supplemented with 20% fetal calf serum.

Results

LAPC-4 cells growing in continuous culture in vitro have retained expression of PSA, androgen receptor, and prostatic acid phosphatase through more than 20 passages. In addition, LAPC-4 cells contain no mutations in either the DNA or ligand binding domains of the androgen receptor, which is a novel characteristic among known prostate cancer models. The only other PSA-expressing cell line, LNCaP, expresses an androgen receptor with a point mutation in the ligand binding domain. In addition, LAPC-4 cells continue to express androgen receptor in androgen independent sublines, analogous to results obtained from the analysis of clinical material. The LAPC-4 cell line is androgen dependent since tumors grow rapidly in male mice but not in female or castrated male mice. The LAPC-4 cell line has remained established for more than 20 passages and has been in continuous culture for over 18 months. These cells continue to express PSA, form tumors in SCID mice, and retain androgen-responsiveness.

Example 10

Testing the Biological Effects of Candidate Genes on Androgen Independent Growth in vivo Some genes upregulated in hormone refractory prostate cancer may contribute to the pathogenesis of androgen independence. Bcl-2, for example, which is upregulated In many advanced prostate cancers, has been demonstrated to confer androgen independence to androgen dependent LNCaP prostate cancer cell line (Raffo et al., 1995). In accordance with this example, one can access in vivo the contribution of candidate genes to the androgen independent phenotype.

LAPC-4 Androgen Dependent Tumor Explants Grow in Tissue Culture and Form Androgen Dependent Tumors upon Reinjection into SCID Mice Current bioassays for androgen dependent and independent growth rely almost exclusively on the LNCaP prostate cancer cell line, because it is the only cell line available which displays features of androgen dependence. In order to circumvent the problem of long-term passaged cell line with the potential for multiple in vitro mutations, the LAPC-4 xenograft was grown in short term culture and then reinjected into mice to form tumors. Explanted tumors were then manipulated genetically and the effects of these manipulations were measured in vivo.

LAPC-4 tumors were minced into small pieces and cultured in media with 15% fetal calf serum. Outgrowth of both epithelial cells and fibroblasts was noted after 2–3 days. Cells then grew to confluence and could be successfully passaged to remove the original tumor pieces. RT-PCR confirmed continued PSA expression. $1 \times 10^7$ cells were then reinjected into either intact male or castrated SCID mice. Similar to the initial experiments, injected cells formed tumors in an androgen dependent fashion, requiring prolonged periods to form tumors in castrated mice.

LAPC-4 Cultures can be Transduced with Retrovirus

In order to test the infectability of explanted LAPC-4 cells by retrovirus, these cells were transduced with a retroviral vector containing a truncated nerve growth factor receptor gene (NGFR). A PG13 packaging cell line, containing the gibbon-ape leukemia virus (GALV) envelope, was used to generate high titer virus. Retrovirus virions produced in this manner have the unique property of infecting human, but not murine. cells, thus avoiding introduction of transgene into mouse stromal cells (Bauer et al., 1995). After infection, the cells were stained with an antibody directed against NGFR and analyzed by FACS analysis. Five–10% of cells were transduced. Murine fibroblasts negative controls showed no infection, while human 293T cells were efficiently transduced.

Biological Assays for cDNAs Upregulated in Androgen-Independent Prostate Cancer

Candidate cDNAs can be cloned into the 5' position of the retroviral vector pSRalpha used extensively in our laboratory (Afar et al., 1994). A reporter gene, either NGFR, LacZ, or human codon-optimized green fluorescent protein (GFP), would be inserted downstream. The plasmid can be transfected into the PG13 packaging cell line, virus collected, and titers measured. LAPC-4 cells can be infected after the first passage and then expanded without selection until sufficient numbers are available for injection. Transgene expression can be confirmed either by FACS analysis or by northern blot analysis using the RDA cDNA clone as a probe.

Two different types of experiments can be performed. In the first, infected cells are injected in to the flanks of intact male SCID mice. After tumors form in both flanks of an individual mouse, one tumor is removed and the mouse is then castrated. The explanted tumor is analyzed to quantify the percentage of cells infected. This can be done either by LacZ straining or by FACS analysis for GFP or NGFR. We anticipate that 5–10% of cells will carry the transgene. The remaining tumor can be similarly analyzed after it regresses and regrows (i.e., about 4–8 weeks after castration). If the transgene confers a survival advantage or androgen independence to infected cells, we would expect to see the percentage of cells carrying the transgene to increase after hormone ablation. Multiple mice can be injected with each construct and positive results confirmed by repetition.

In a second set of experiments, one can implant infected cells into intact and castrated male mice in parallel after quantifying infection frequency. Resulting tumors (at 4 and 12 weeks, respectively) are analyzed for insert frequency as described above. Again, we expect that "androgen independent" genes will provide an androgen independent growth advantage and predominate in the resulting tumor. In addition, it is possible that a given candidate gene will shorten the time to tumor formation in castrated males. This can also be measured. Finally, it is possible that a given gene could cause aggressive androgen dependent growth. This too can be quantified in this assay, by comparing time to tumor formation and insert frequency before and after injection into intact male mice.

These assays can be validated with positive controls. In particular, one can use bcl-2, c-myc, and c-met, since these have been consistently associated with androgen independence.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

References

Aldrovani, G. M. et al. The SCID-hu mouse as a model for HIV-1 infection. Nature 363: 732–736 (1993).

Baston, O. V. The role of the vertebral veins in metastatic processes. Ann Int. Med. 16: 38–45 (1942).

Berettoni, B. A. and Carter, J. R. Mechanisms of cancer metastasis to bone. J. Bone Joint Surg. 68A: 308–312 (1986).

Brandt, B. et al. Isolation of prostate-derived single cells and cell clusters from human peripheral blood. Cancer Res. 56: 4556–4561 (1996).

Coman, D. R. and DeLong, R. P. The role of the vertebral venous system in the metastasis of cancer to the spinal column. Cancer 4: 610–618 (1951).

Deguchi, T. et al. Detection of micrometastatic prostate cancer cells in the bone marrow of patients with prostate cancer. Brit. J. Cancer 75: 634–638 (1997).

Fidler, I. J. Critical factors in the biology of human cancer metastasis. Cancer Res. 50 6130–6138 (1990).

Ghossein, R. A. et al. Detection of circulating tumor cells in patients with localized and metastatic prostate carcinoma: Clinical implications. *J. Clin. Oncol.* 13: 1195–2000 (1995).

Gleave, M. E. et al. Serum prostate specific antigen levels in mice bearing human prostate LNCaP tumors are determined tumor volume and endocrine and growth factors. Cancer Res. 52: 1598–1605 (1992).

Haq, M et al. Rat prostate adenocarcinoma cells disseminate to bone and adhere preferentially to bone marrow-derived endothelial cells. Cancer Res. 52: 4613–4619 (1992).

Hsu, S. M. et al. A comparative study of the peroxidase-antiperoxidase method and an avidin-biotin complex method for studying polypeptide hormones with radioimmunoassay antibodies. Am J. Clin. Pathol. 75: 734–738 (1981).

Kaighn, M. E. et al. Establishment and characterization of a prostatic carcinoma cell line. Invest. Urol. 17: 16–23 (1979).

Karp, J. E., et al. Prostate cancer Prevention: Investigational approaches and opportunities. Cancer Res. 56: 5547–5556 (1996).

Katz, A. E. et al. Molecular staging of prostate cancer with the use of an enhanced reverse transcriptase-PCR assay. Urology 43: 765–775 (1994).

Katz, A. E. et al. The role of reverse-transcriptase polymerase chain reaction assay for prostate-specific antigen in the selection of patients for radical prostatectomy. Urology Clinics of North America 23: 541–549 (1996).

Kozlowski, J. M. et al. Prostate cancer and the invasive phenotype: Application of new in vivo and in vitro approaches. In: Tumor Progression and Metastasis, edited by Fidler. I. J. and Nicholson, G. Alan R. Liss, Inc., New York, 1988, p. 189–231.

Lee, C. et al. In vitro and in vivo approaches to study metastasis in human prostatic cancer. Canc. Met. Rev. 12: 21–28 (1993).

Lim, D. J. et al. Growth of an androgen-sensitive human prostate cancer cell line. LNCaP in nude mice. Prostate 22: 109–118 (1993).

Liu, A. Y. et al. Prostatic cell lineage markers: Emergence of BCL2+ cells of human prostate cancer xenograft LuCaP 23 following castration. Intl. J. Cancer 65: 85–89 (1996).

Maricelli, M. et al. Definition of the human androgen receptor gene structure permits the identification of mutations that cause androgen resistance: Premature termination of the receptor protein at amino acid residue 588 cause complete androgen resistance. Mol. Endocrinol. 909: 1105–1116 (1990).

Melchior, S. W. et al. Clinical relevance of prostate cells in the bone marrow of patients with clinically localized carcinoma of the prostate (CAP). J. Urology 157: 1718 (1997) (Abstract).

Netland, P. A. and Zetter, B. R. Metastatic potential of B16 melanoma cells after in vitro selection for organ-specific adherence. J. Cell Biol. 10: 720–724 (1985).

Nishijima, Y. et al. Clinical significance of the vertebral vein in prostate cancer metastasis. Adv. Exp. Med. Biol. 324: 93–100 (1992).

Noel, A. et al. Basement membrane components (Matrigel) promote the tumorigenicity of human breast adenocarcinoma MCF7 cells and provide an in vivo model to assess the responsiveness of cells to estrogen. Biochemical Pharmacology 43: 1263–1267 (1992).

Olsson, C. A. et al. Reverse transcriptase-polymerase chain reaction assays for prostate cancer. Urology Clinics of North America 24: 367–378 (1997).

Pang, S. et al. Prostate tissue specificity of the prostate-specific antigen romoter isolated from a patient with prostate cancer. Hum. Gene Ther. 6: 1417–1426 (1995).

Pretlow, T. G. et al. Transplantation of human prostatic adenocarcinoma into nude mice in Matrigel. Cancer Res. 51: 3814–3817 (1991).

Saiki, R. K., et al. Enzymatic amplification of β-globin genomic sequences and restriction site analysis for diagnosis of sickle cell anemia. Science 230: 1350–1354 (1895).

Sambrook, J. et al. Molecular Cloning: A Laboratory Manual, Ed.2. Cold Spring Harbor Press, Clod Spring Harbor, N.Y., 1989.

Seiden, M. V. et al. Detection of circulating tumor cells in men with localized prostate cancer. J. Clin. Oncol. 12: 2364–2639 (1994).

Shevrin, D. H. et al. Development of skeletal metastasis by human prostate cancer in athymic nude mice. Clin. Exp. Metastasis 6: 401–409 (1988).

Shevrin, D. H. et al. Patterns of metastasis by the human prostate cancer cell line PC-3 in athymic nude mice. The Prostate 15: 187–194 (1989).

Sutherland, R. W. et al. androgen receptor gene mutations are rarely associated with isolated penile hypospadias. J. Urol. 156: 828–831 (1996).

Thalmann, G. N. et al. Androgen-independent cancer progression and bone metastasis in the LNCaP model of human prostate cancer. Cancer Res. 54: 2577–2581 (1994).

Wang, M. and Stearns, M. E. Isolation and characterization of 3 PC-3 prostatic tumor sublines which preferentially metastasize to select organs in SCID mice. Differentiation 48: 115–125 (1991).

Wainstein, M. A. et al. Androgen-Dependent xenograft model derived from a primary human prostatic carcinoma. Cancer Res. 54: 6049–6052 (1994).

Wood, D. P. et al. Identification of bone marrow micrometastases in patients with prostate cancer. Cancer 74: 2533–2540 (1994).

Zetter, B. R. et al. The cellular basis for prostate cancer metastasis. Adv. Exp. Med. Biol. 324: 39–43 (1992).

What is claimed is:

1. A mouse model of human prostate cancer, said mouse model comprising a human androgen-dependent prostate cancer xenograft of locally advanced or metastatic prostate cancer or a cell suspension thereof, wherein the mouse model exhibits the transition from androgen-dependence to androgen-independence, and recapitulates the development of primary tumors, micrometastasis, or formation of osteoblastic lesions characteristic of late stage prostate cancer.

2. The mouse model of human prostate cancer of claim 1, wherein the mouse is a SCID mouse.

3. The mouse model of claim 1, wherein the xenograft is implanted subcutaneously.

4. The mouse model of claim 1, wherein the xenograft is implanted intraprostatically.

5. The mouse model of claim 1, wherein the xenograft is implanted within a bone of the mouse.

6. The mouse model of claim 1, wherein the xenograft is derived from an explant selected from prostate, lymph node, lung or bone tissue.

* * * * *

UNITED STATES PATENT AND TRADEMARK OFFICE
CERTIFICATE OF CORRECTION

PATENT NO. : 6,828,471 B2 Page 1 of 1
DATED : December 7, 2004
INVENTOR(S) : Charles L. Sawyers et al.

It is certified that error appears in the above-identified patent and that said Letters Patent is hereby corrected as shown below:

Column 1,
Line 17, before "BACKGROUND OF THE INVENTION" insert the following section:
-- STATEMENT AS TO RIGHTS TO INVENTIONS MADE UNDER
    FEDERALLY SPONSORED RESEARCH OR DEVELOPMENT
This invention was made with Government support under Grant No. GM-08243, awarded by the National Institutes of Health. The Government has certain rights in this invention. --

Signed and Sealed this

First Day of March, 2005

JON W. DUDAS
*Director of the United States Patent and Trademark Office*